(12) United States Patent  (10) Patent No.: US 8,313,487 B2
Tyber et al.  (45) Date of Patent: Nov. 20, 2012

(54) FIXATION SYSTEM, AN INTRAMEDULLARY FIXATION ASSEMBLY AND METHOD OF USE

(75) Inventors: Jeff Tyber, Bethlehem, PA (US); Jamy Gannoe, West Milford, NJ (US); Chris Digiovanni, Barrington, RI (US); Brian Gerard Donley, Solon, OH (US)

(73) Assignee: Extremity Medical LLC, Parsippany, NJ (US)

( * ) Notice: Subject to any disclaimer, the term of this patent is extended or adjusted under 35 U.S.C. 154(b) by 0 days.

(21) Appl. No.: 12/658,699

(22) Filed: Feb. 11, 2010

(65) Prior Publication Data

US 2010/0256639 A1  Oct. 7, 2010

Related U.S. Application Data

(63) Continuation-in-part of application No. 12/460,069, filed on Jul. 13, 2009, and a continuation-in-part of application No. 12/456,808, filed on Jun. 23, 2009.

(60) Provisional application No. 61/132,932, filed on Jun. 24, 2008.

(51) Int. Cl.
*A61B 17/56* (2006.01)
(52) U.S. Cl. .......................... 606/62; 606/64
(58) Field of Classification Search .............. 606/62–68, 606/280, 283
See application file for complete search history.

(56) References Cited

U.S. PATENT DOCUMENTS

| | | | |
|---|---|---|---|
| 2,580,821 A | 1/1952 | Nicola | |
| 3,924,276 A | 12/1975 | Eaton | |
| 4,152,533 A | 5/1979 | Gazda | |
| 4,381,770 A | 5/1983 | Neufeld | |
| 4,465,065 A | 8/1984 | Gotfried | |
| 4,854,797 A | 8/1989 | Gourd | |
| 4,940,467 A | 7/1990 | Tronzo | |
| 4,947,502 A | 8/1990 | Engelhardt | |
| 5,112,333 A | 5/1992 | Fixel | |
| 5,163,940 A | 11/1992 | Bourque | |
| 5,350,380 A | 9/1994 | Goble et al. | |
| 5,403,321 A | 4/1995 | DiMarco | |
| 5,454,267 A | 10/1995 | Moreau et al. | |
| 5,456,267 A | 10/1995 | Stark | |
| 5,478,341 A | 12/1995 | Cook et al. | |
| 5,505,731 A | 4/1996 | Tornier | |
| 5,531,748 A | 7/1996 | de la Caffiniere | |
| 5,540,694 A | 7/1996 | DeCarlo, Jr. et al. | |
| 5,573,538 A | 11/1996 | Laboureau | |
| 5,601,550 A | 2/1997 | Esser | |
| 5,613,971 A | 3/1997 | Lower et al. | |
| 5,620,449 A | 4/1997 | Faccioli et al. | |

(Continued)

FOREIGN PATENT DOCUMENTS

WO  WO 2006116164  11/2006

(Continued)

*Primary Examiner* — Eduardo C Robert
*Assistant Examiner* — Stuart S Bray
(74) *Attorney, Agent, or Firm* — Ward & Zinna, LLC

(57) ABSTRACT

An intramedullary fixation assembly for bone fusion includes a first member positioned at a proximal end of the intramedullary fixation assembly, where the first member includes a plurality of first and second retaining screws, and a second member positioned at a distal end of the intramedullary fixation assembly, where the second member includes a plurality of third and fourth retaining screws. The first member is slideably coupled to the second member and provides for an interference fit with the second member.

24 Claims, 25 Drawing Sheets

U.S. PATENT DOCUMENTS

| | | | |
|---|---|---|---|
| 5,702,470 A | 12/1997 | Menon | |
| 5,718,705 A | 2/1998 | Sammarco | |
| 5,741,266 A | 4/1998 | Moran et al. | |
| 5,766,221 A | 6/1998 | Benderev et al. | |
| 5,779,704 A | 7/1998 | Kim | |
| 5,888,203 A | 3/1999 | Goldberg | |
| 5,891,150 A | 4/1999 | Chan | |
| 5,968,050 A | 10/1999 | Torrie | |
| 5,984,681 A | 11/1999 | Huang | |
| D420,132 S | 2/2000 | Bucholz et al. | |
| 6,019,761 A | 2/2000 | Gustillo | |
| 6,106,528 A | 8/2000 | Durham et al. | |
| 6,120,511 A | 9/2000 | Chan | |
| 6,123,709 A | 9/2000 | Jones | |
| 6,126,661 A | 10/2000 | Faccioli et al. | |
| 6,168,595 B1 | 1/2001 | Durham et al. | |
| 6,221,074 B1 | 4/2001 | Cole et al. | |
| 6,235,031 B1 | 5/2001 | Hodgeman et al. | |
| 6,254,605 B1 | 7/2001 | Howell | |
| 6,254,606 B1 | 7/2001 | Carney et al. | |
| 6,261,290 B1 | 7/2001 | Friedl | |
| 6,270,499 B1 | 8/2001 | Leu et al. | |
| 6,280,442 B1 | 8/2001 | Barker et al. | |
| 6,287,313 B1 | 9/2001 | Sasso | |
| 6,402,753 B1 | 6/2002 | Cole et al. | |
| 6,458,134 B1 | 10/2002 | Songer et al. | |
| 6,517,541 B1 | 2/2003 | Sesic | |
| 6,527,775 B1 | 3/2003 | Warburton | |
| 6,562,046 B2 | 5/2003 | Sasso | |
| 6,569,165 B2 | 5/2003 | Wahl et al. | |
| 6,626,916 B1 | 9/2003 | Yeung et al. | |
| 6,629,976 B1 | 10/2003 | Gnos et al. | |
| 6,648,889 B2 | 11/2003 | Bramlet et al. | |
| 6,669,700 B1 | 12/2003 | Farris et al. | |
| 6,679,888 B2 | 1/2004 | Green et al. | |
| 6,692,496 B1 | 2/2004 | Wardlaw | |
| 6,692,503 B2 | 2/2004 | Foley et al. | |
| 6,709,436 B1 | 3/2004 | Hover et al. | |
| 6,712,849 B2 | 3/2004 | Re et al. | |
| 6,793,659 B2 | 9/2004 | Putnam | |
| 6,808,527 B2 | 10/2004 | Lower et al. | |
| 6,849,093 B2 | 2/2005 | Michelson | |
| 6,951,538 B2 | 10/2005 | Ritland | |
| 6,951,561 B2 | 10/2005 | Warren et al. | |
| 7,018,380 B2 | 3/2006 | Cole | |
| 7,041,104 B1 | 5/2006 | Cole et al. | |
| 7,063,724 B2 | 6/2006 | Re et al. | |
| 7,074,221 B2 | 7/2006 | Michelson | |
| 7,144,399 B2 | 12/2006 | Hayes et al. | |
| 7,160,302 B2 | 1/2007 | Warburton | |
| 7,175,632 B2 | 2/2007 | Singhatat et al. | |
| 7,229,448 B2 | 6/2007 | Goble et al. | |
| 7,232,442 B2 | 6/2007 | Sohngen et al. | |
| 7,247,156 B2 | 7/2007 | Ekholm et al. | |
| 7,267,678 B2 | 9/2007 | Medoff | |
| 7,326,248 B2 | 2/2008 | Michelson | |
| 7,341,588 B2 | 3/2008 | Swanson | |
| 7,344,538 B2 | 3/2008 | Myerson et al. | |
| 7,410,488 B2 | 8/2008 | Janna et al. | |
| 7,524,326 B2 | 4/2009 | Dierks | |
| 7,527,627 B2 | 5/2009 | Ferrante et al. | |
| 7,588,577 B2 | 9/2009 | Fencl et al. | |
| 7,601,153 B2 * | 10/2009 | Shinjo et al. | 606/64 |
| 7,632,272 B2 | 12/2009 | Munro et al. | |
| 7,655,009 B2 | 2/2010 | Grusin | |
| 7,670,340 B2 * | 3/2010 | Brivio et al. | 606/64 |
| 7,713,271 B2 | 5/2010 | Warburton | |
| 7,731,721 B2 | 6/2010 | Rathbun et al. | |
| 7,763,021 B2 | 7/2010 | Cole et al. | |
| 7,763,022 B2 | 7/2010 | Speitling et al. | |
| 7,763,023 B2 | 7/2010 | Gotfried | |
| 7,771,428 B2 | 8/2010 | Siravo et al. | |
| 7,785,326 B2 | 8/2010 | Green et al. | |
| 7,799,061 B2 | 9/2010 | Kay et al. | |
| 7,815,646 B2 | 10/2010 | Hart | |
| 7,842,036 B2 | 11/2010 | Phillips | |
| 7,867,231 B2 | 1/2011 | Cole | |
| 7,892,234 B2 | 2/2011 | Schlienger et al. | |
| 7,892,264 B2 | 2/2011 | Sanders et al. | |
| 7,909,825 B2 | 3/2011 | Saravia et al. | |
| 7,914,532 B2 | 3/2011 | Shaver et al. | |
| 7,918,853 B2 | 4/2011 | Watanabe et al. | |
| 7,922,748 B2 | 4/2011 | Hoffman | |
| 7,927,340 B2 | 4/2011 | Hart | |
| 7,938,848 B2 | 5/2011 | Sweeney | |
| 7,947,043 B2 | 5/2011 | Mutchler | |
| 8,034,056 B2 | 10/2011 | Fencl et al. | |
| 8,034,082 B2 | 10/2011 | Lee et al. | |
| 8,057,476 B2 | 11/2011 | Ekholm et al. | |
| 8,092,453 B2 | 1/2012 | Warburton | |
| 8,100,910 B2 | 1/2012 | Warburton | |
| 8,100,946 B2 | 1/2012 | Strausbaugh et al. | |
| 2002/0052605 A1 | 5/2002 | Grooms et al. | |
| 2002/0143333 A1 | 10/2002 | von Hoffmann et al. | |
| 2002/0169453 A1 | 11/2002 | Berger | |
| 2003/0060827 A1 | 3/2003 | Coughlin | |
| 2003/0065391 A1 | 4/2003 | Re et al. | |
| 2003/0083667 A1 | 5/2003 | Ralph et al. | |
| 2004/0082959 A1 | 4/2004 | Hayes et al. | |
| 2004/0172031 A1 | 9/2004 | Rubecamp et al. | |
| 2004/0181234 A1 | 9/2004 | McDevitt et al. | |
| 2004/0220570 A1 | 11/2004 | Frigg | |
| 2005/0015092 A1 | 1/2005 | Rathbun et al. | |
| 2005/0069397 A1 | 3/2005 | Shavit et al. | |
| 2005/0107791 A1 | 5/2005 | Manderson | |
| 2005/0171544 A1 | 8/2005 | Falkner, Jr. | |
| 2005/0192580 A1 | 9/2005 | Dalton | |
| 2005/0251147 A1 | 11/2005 | Novak | |
| 2005/0273101 A1 | 12/2005 | Schumacher | |
| 2005/0277940 A1 | 12/2005 | Neff | |
| 2005/0283159 A1 | 12/2005 | Amara | |
| 2006/0009774 A1 | 1/2006 | Goble et al. | |
| 2006/0009846 A1 | 1/2006 | Trieu et al. | |
| 2006/0015101 A1 | 1/2006 | Warburton et al. | |
| 2006/0095039 A1 * | 5/2006 | Mutchler | 606/64 |
| 2006/0122600 A1 | 6/2006 | Cole | |
| 2006/0142770 A1 | 6/2006 | Capanni | |
| 2006/0149244 A1 | 7/2006 | Amrein et al. | |
| 2006/0189991 A1 | 8/2006 | Bickley | |
| 2006/0200143 A1 | 9/2006 | Warburton | |
| 2006/0200144 A1 | 9/2006 | Warburton | |
| 2006/0200160 A1 | 9/2006 | Border et al. | |
| 2006/0206044 A1 | 9/2006 | Simon | |
| 2006/0235396 A1 | 10/2006 | Sanders et al. | |
| 2006/0241608 A1 | 10/2006 | Myerson et al. | |
| 2006/0241777 A1 | 10/2006 | Partin et al. | |
| 2006/0264954 A1 | 11/2006 | Sweeney, II et al. | |
| 2007/0021839 A1 | 1/2007 | Lowe | |
| 2007/0038306 A1 | 2/2007 | O'Gara | |
| 2007/0055286 A1 | 3/2007 | Ralph et al. | |
| 2007/0066977 A1 | 3/2007 | Assell et al. | |
| 2007/0073290 A1 | 3/2007 | Boehm, Jr. | |
| 2007/0093841 A1 | 4/2007 | Hoogland | |
| 2007/0112432 A1 | 5/2007 | Reiley | |
| 2007/0173835 A1 | 7/2007 | Medoff | |
| 2007/0233114 A1 | 10/2007 | Bouman | |
| 2007/0270848 A1 * | 11/2007 | Lin | 606/65 |
| 2007/0270855 A1 | 11/2007 | Partin | |
| 2008/0065224 A1 | 3/2008 | Reigstad et al. | |
| 2008/0091203 A1 | 4/2008 | Warburton et al. | |
| 2008/0154271 A1 | 6/2008 | Berberich et al. | |
| 2008/0208261 A1 | 8/2008 | Medoff | |
| 2008/0269908 A1 | 10/2008 | Warburton | |
| 2008/0294164 A1 * | 11/2008 | Frank et al. | 606/64 |
| 2008/0306401 A1 | 12/2008 | Hart | |
| 2008/0306537 A1 | 12/2008 | Culbert | |
| 2009/0018542 A1 | 1/2009 | Saravia et al. | |
| 2009/0048600 A1 * | 2/2009 | Matityahu et al. | 606/62 |
| 2009/0062797 A1 | 3/2009 | Huebner et al. | |
| 2009/0088767 A1 | 4/2009 | Leyden et al. | |
| 2009/0088804 A1 | 4/2009 | Kyle et al. | |
| 2009/0088806 A1 | 4/2009 | Leyden et al. | |
| 2009/0093813 A1 | 4/2009 | Elghazaly | |
| 2009/0093849 A1 | 4/2009 | Grabowski | |
| 2009/0099571 A1 | 4/2009 | Cresina et al. | |
| 2009/0149857 A1 | 6/2009 | Culbert et al. | |
| 2009/0157077 A1 | 6/2009 | Larsen et al. | |

| | | |
|---|---|---|
| 2009/0157078 A1 | 6/2009 | Mikol |
| 2009/0157079 A1 | 6/2009 | Warburton et al. |
| 2009/0157080 A1 | 6/2009 | Warburton |
| 2009/0177203 A1 | 7/2009 | Reiley |
| 2009/0209961 A1 | 8/2009 | Ferrante et al. |
| 2009/0240252 A1 | 9/2009 | Chang |
| 2009/0248025 A1 | 10/2009 | Haidukewych et al. |
| 2009/0264885 A1* | 10/2009 | Grant et al. .............. 606/66 |
| 2009/0292292 A1 | 11/2009 | Fencl et al. |
| 2009/0306666 A1 | 12/2009 | Czartoski et al. |
| 2009/0326534 A1 | 12/2009 | Yamazaki et al. |
| 2010/0023011 A1* | 1/2010 | Nakamura .............. 606/64 |
| 2010/0030280 A1 | 2/2010 | Jackson |
| 2010/0174284 A1 | 7/2010 | Schwammberger et al. |
| 2010/0179551 A1 | 7/2010 | Keller et al. |
| 2010/0234846 A1 | 9/2010 | Eglseder |
| 2010/0312279 A1 | 12/2010 | Gephart et al. |
| 2011/0004255 A1 | 1/2011 | Weiner et al. |
| 2011/0022066 A1 | 1/2011 | Sevrain |
| 2011/0046681 A1 | 2/2011 | Prandi et al. |
| 2011/0060337 A1 | 3/2011 | Ferrante et al. |
| 2011/0137313 A1 | 6/2011 | Jensen et al. |
| 2011/0144645 A1 | 6/2011 | Saravia et al. |
| 2011/0160729 A1 | 6/2011 | Overes et al. |

FOREIGN PATENT DOCUMENTS

WO    WO 2007131287    11/2007

* cited by examiner

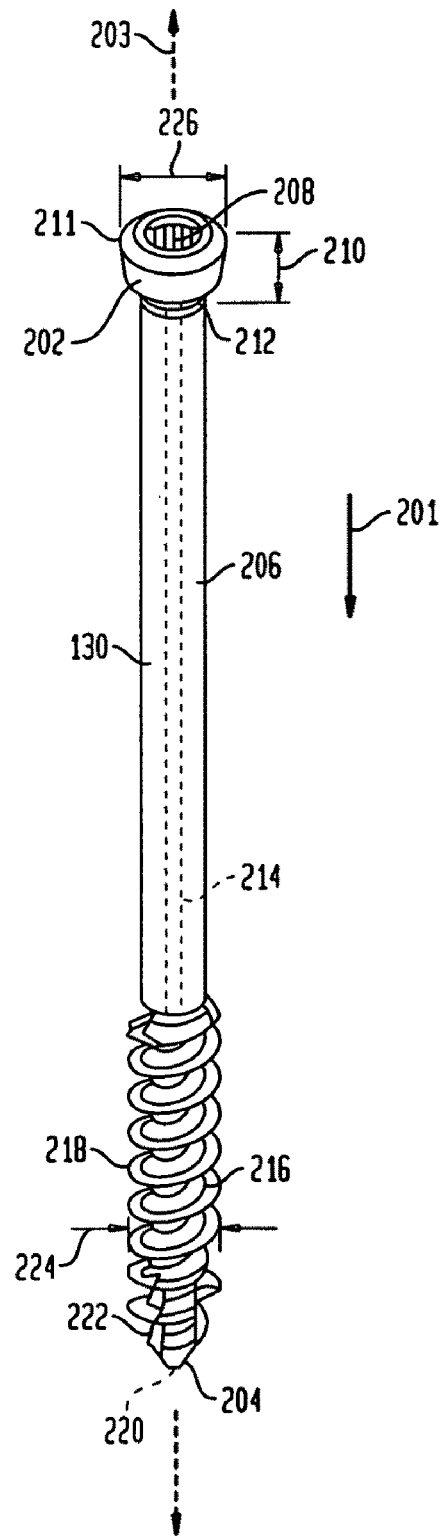

FIXATION SYSTEM, AN INTRAMEDULLARY FIXATION ASSEMBLY AND METHOD OF USE

CROSS-REFERENCE TO RELATED APPLICATIONS

This continuation-in-part application claims the benefit of Non-Provisional application Ser. No. 12/460,069, filed Jul. 13, 2009, and Non-Provisional application Ser. No. 12/456,808, filed Jun. 23, 2009, both of which are continuation applications of provisional Application No. 61/132,932, filed Jun. 24, 2008, the entire contents of the entire chain of applications are herein incorporated by reference.

FIELD OF THE INVENTION

This invention relates to the field of orthopedic implant devices, and more particularly, to an intramedullary fixation assembly used for fusion of the angled joints, bones and deformity correction, such as the metatarsal and phalangeal bones in the foot.

BACKGROUND OF THE INVENTION

Orthopedic implant devices, such as intramedullary plates, rods and screws are often used to repair or reconstruct bones and joints affected by trauma, degeneration, deformity and disease, such as Charcot arthropathy caused by diabetes in some patients, Hallux Valgus deformities, failed Keller Bunionectomies, Rheumatoid Arthritis, and severe deformities. Charcot arthropathy (or Charcot foot) is a destructive process affecting many regions including joints of the foot and ankle in diabetics. This condition causes bony fragmentation, dislocation, and fractures that eventually progresses to foot deformity, bony prominences, ulceration and instability of the foot. Charcot arthropathy can affect any joint in the body but is often seen in the feet affecting the metatarsal, tarsometatarsal and tarsal joints and frequently causes the foot to lose its arch or curvature, thus resulting in "flat footedness" in the mid-foot region.

Early treatment for Charcot foot includes the use of therapeutic footwear, immobilization of the foot and/or non-weight bearing treatment. Surgical treatments include orthopedic fixation devices that fixate the bones in order to fuse them into a stable mass. These orthopedic implant devices realign bone segments and hold them together in compression until healing occurs, resulting in a stable mass.

In order to restore an arch in a Charcot foot, the physician must estimate the arch and manually align the bones and deliver the screws to hold the bones in place, while reducing bone purchase. Intramedullary nails and/or a plate with a lag screw too have deficiencies. These intramedullary nails also do not reconstruct an arch that is lost due to Charcot foot disease.

Moreover, infections and wound complications are a major concern in the aforementioned procedures. Wound closure is technically demanding for the surgeon, and devices that add surface prominence, such as plates or exposed screws, add to the difficulty by requiring greater tissue tension during incision reapproximation. This increases the risk of postoperative wound infections and dehiscence that may ultimately result in limb amputation.

Various implants have been utilized for surgical treatment of these bones and joints, including bone screws. Implants have also been utilized to treat severe deformities in the metatarsal and phalangeal bones, including multiple screws and plates. These multiple screws and plate implants have been commonly used in a first metatarsal-phalangeal fusion procedure to fuse the first metatarsal to the first phalangeal bone in hallux valgus deformities, failed keller bunionectomies, rheumatoid arthritis, and other types of severe deformities in the metatarsal and phalange bones. While these devices allow fixation and promote fusion, they do not deliver restoration of the arch in a Charcot foot nor are they effective in metatarsal-phalangeal (MTP) fusion procedures.

Particularly, screw implants in MTP procedures are ineffective in delivering sufficient compression to the bones in the foot, preventing screw head break out, or delivering effective bending resistance. Moreover, hard to control dorsiflexion and valgus angles as well skin irritation from proximity to the skin prevents these screw implants from being readily utilized for surgical treatment. Yet further, plate implants used with bone screws too have the same drawbacks as fixed varus and valgus angles, lack of direct compression across the MTP joint, and skin irritations from proximity to the skin reduce the effectiveness of these implants.

There is therefore a need for an intramedullary fixation assembly and method of use that overcomes some or all of the previously delineated drawbacks of prior fixation assemblies.

SUMMARY OF THE INVENTION

An object of the invention is to overcome the drawbacks of previous inventions.

Another object of the invention is to provide a novel and useful intramedullary fixation assembly that may be utilized to treat bones in a mid-foot and forefoot regions.

Another object of the invention is to restore the arch by utilizing an intramedullary assembly.

Another object of the invention is to provide a system for treating deteriorating bones in a mid-foot region.

Another object of the invention is to provide a method for restoring the arch of the foot by delivering a fixator that can be coupled in a patient's foot.

Another object of the invention is to fuse the metatarsal phalangeal joint by utilizing an intramedullary assembly.

In a first non-limiting aspect of the invention, a fixation assembly comprising two members is provided. A first member is positioned at a proximal end of the intramedullary fixation assembly, with the first member including a plurality of first and second retaining screws. A second member is positioned at a distal end of the intramedullary fixation assembly, where the second member includes a plurality of third and fourth retaining screws. The first member is slideably coupled to the second member and provides for an interference fit with the second member.

In a second non-limiting aspect of the invention, a method for bone fusion comprises seven steps. Step one includes providing a fixation assembly, where the fixation assembly includes a proximal member for connecting to each of the medial cuneiform, navicular, and talus bones and a distal member for connecting to a metatarsal bone. Step two includes making a dorsal incision, and drilling the intramedullary canals of the metatarsal, medial cuneiform, navicular, and talus bones. Step four includes reaming the metatarsal intramedullary canal and inserting the distal member. Step five includes aligning the distal member and inserting retaining screws into the distal member. Step six includes reaming the medial cuneiform, navicular, and talus bones. Step seven includes inserting the proximal member into the distal member and into the intramedullary canal of the medial cuneiform bone. Step seven includes aligning the proximal member 1810 and inserting retaining into the talus bone and into the proximal member.

BRIEF DESCRIPTION OF THE DRAWINGS

A further understanding of the invention can be obtained by reference to a preferred embodiment set forth in the illustrations of the accompanying drawings. Although the illustrated embodiment is merely exemplary of systems and methods for carrying out the invention, both the organization and method of operation of the invention, in general, together with further objectives and advantages thereof, may be more easily understood by reference to the drawings and the following description. The drawings are not intended to limit the scope of this invention, which is set forth with particularity in the claims as appended or as subsequently amended, but merely to clarify and exemplify the invention.

For a more complete understanding of the invention, reference is now made to the following drawings in which:

FIG. 2 is a perspective view of a proximal screw member used in the fixation system shown in FIG. 1 according to the preferred embodiment of the invention.

DETAILED DESCRIPTION

The invention may be understood more readily by reference to the following detailed description of preferred embodiment of the invention. However, techniques, systems and operating structures in accordance with the invention may be embodied in a wide variety of forms and modes, some of which may be quite different from those in the disclosed embodiment. Consequently, the specific structural and functional details disclosed herein are merely representative, yet in that regard, they are deemed to afford the best embodiment for purposes of disclosure and to provide a basis for the claims herein, which define the scope of the invention. It must be noted that, as used in the specification and the appended claims, the singular forms "a", "an", and "the" include plural referents unless the context clearly indicates otherwise.

Figure 1:
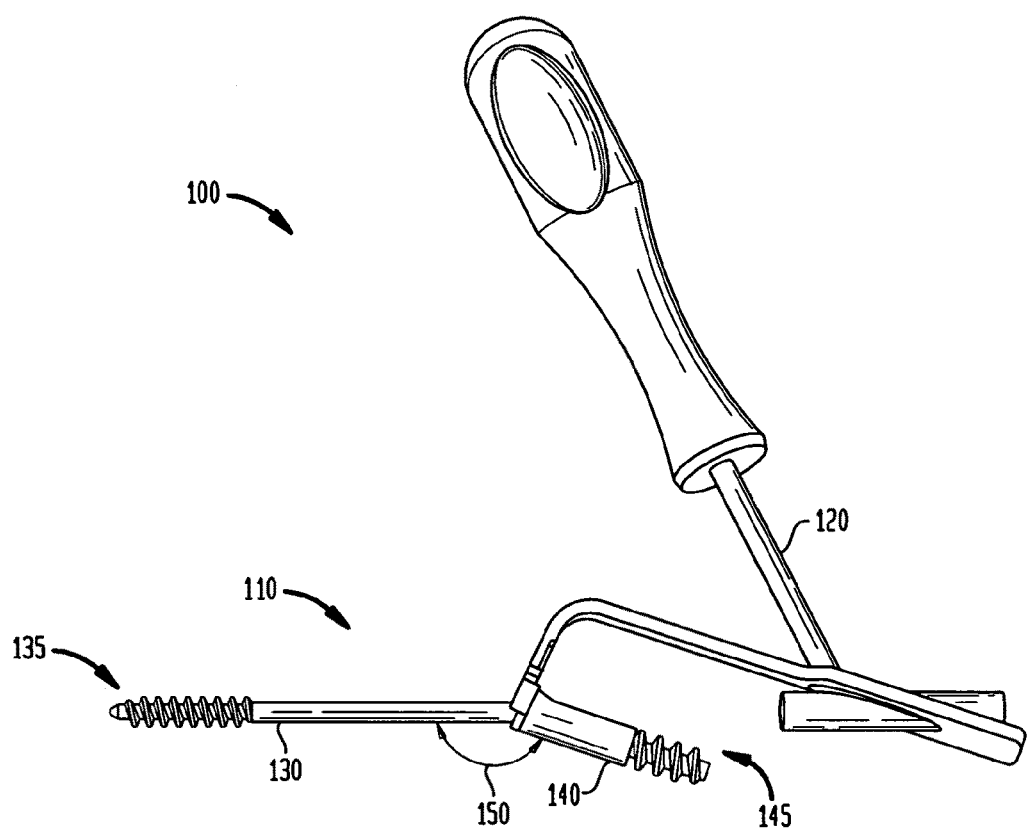
FIG. 1 is a perspective view of a fixation system according to a preferred embodiment of the invention.

Referring now to FIG. 1, there is shown a fixation system 100 which is made in accordance with the teachings of the preferred embodiment of the invention. As shown, the fixation system 100 includes an intramedullary fixation assembly 110, comprising a proximal screw member 130 and a distal member 140. Proximal screw member 130 is provided on proximal end 135 of assembly 110 and is coupled to a distal member 140 that is provided on the distal end 145 of the fixation assembly 110. Also, proximal screw member 130 makes a fixed angle 150 with distal member 140 and this angle 150 determines the angle for arch restoration. Moreover, fixation system 100 includes instrument 120 that is utilized to couple intramedullary fixation assembly 110 to the bones in the mid-foot region (not shown). It should be appreciated that in one non-limiting embodiment, intramedullary fixation assembly 110 may be made from a Titanium material, although, in other non-limiting embodiments, intramedullary fixation assembly 110 may be made from SST, PEEK, NiTi, Cobalt chrome or other similar types of materials.

As shown in FIG. 2, proximal screw member 130 is generally cylindrical in shape and extends from first bulbous portion 202 to second tapered end 204. End 204 has a diameter that is slightly smaller than diameter 226 of bulbous portion 202. Additionally, bulbous portion 202 has a taper, such as a Morse taper, with a width that decreases from end 211 to end 212. The taper allows for a locked interference fit with tapered aperture 316 when tapered bulbous portion 202 is combined with tapered aperture 316, shown and described below. Moreover, bulbous portion 202 is generally circular and has a generally hexagonal torque transmitting aperture 208 that traverses length 210 of bulbous portion 202. However, a star-shaped aperture, a square-shaped aperture, or any other shaped aperture may be utilized without departing from the scope of the invention. Torque transmitting aperture 208 is utilized to transmit a torque from bulbous portion 202 to tapered end 204 by rotating bulbous portion 202.

Further, proximal screw member 130 has a first smooth exterior portion 206 extending from end 212 of bulbous portion 202. Portion 206 comprises an internal aperture 214 that longitudinally traverses portion 206 in direction 201. Portion 206 terminates into a second generally tubular portion 216. Portion 216 may comprise internal circular aperture 220 that longitudinally traverses inside portion 216. Internal circular aperture 220 is aligned with apertures 214 and 208 along axis 203 to form a continuous opening (i.e., a cannula) from bulbous portion 202 to end 204. The continuous opening or cannula is provided to interact with a guide wire (not shown) by receiving the guide wire within the continuous opening thereby positioning and locating the proximal member 130. In other non-limiting embodiments, the proximal member 130 may be provided without apertures 220 and 214 (i.e., the proximal member is solid).

Furthermore, tubular portion 216 has a plurality of circular threads, such as threads 218, which are circumferentially disposed on the external surface of portion 216 and, with threads 218 having an external diameter 224. Portion 216 may also be provided with a self-tapping leading edge 222 to provide portion 216 with the ability to remove bone material during insertion of proximal screw member 130 into bone. It should be appreciated that the length of the proximal member 130 may be selected of varying lengths to allow a surgeon to fuse different joints in-a foot (not shown).

Figure 3A:
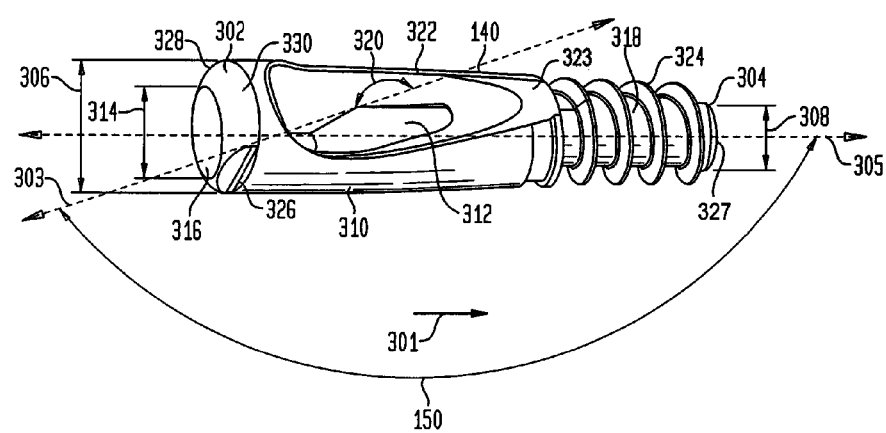
FIG. 3A is a perspective view of a distal member used in the fixation system shown in FIG. 1 according to the preferred embodiment of the invention.
Figure 3B:
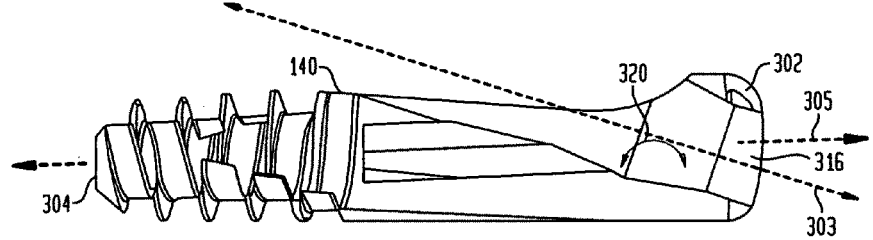
FIG. 3B is a perspective cross-sectional view of the distal member shown in FIG. 3A according to the preferred embodiment of the invention.

As shown in FIGS. 3A-3B, distal member 140 of the preferred embodiment is generally tubular in shape and tapers from a first end 302 to a second end 304 (i.e. end 302 has a diameter 306 that is slightly larger than diameter 308 of end 304). However, in another non-limiting embodiment, distal member 140 has a constant width from first end 302 to second end 304. Further, first end 302 is generally semi-spherical in shape and has an internal circular aperture 316, which traverses end 302 along direction 301 (i.e. end 302 is generally "donut" shaped). Additionally, circular aperture 316 emanates from surface 322, such that portion 310 has a generally tapered aperture 316 provided in portion 310. Circular aperture 316 comprises slope 320 from first end 302 to end 323 of portion 310. Further, aperture 316 is aligned along axis 303, which is offset from horizontal axis 305 of distal member 140. Axis 303 forms an angle 150 with horizontal axis 305 that determines the angle for arch restoration, as shown in FIG. 3A. Angle 150 may be any angle greater than 90 degrees and less than 180 degrees. Tapered aperture 316 when combined with tapered bulbous portion 202, shown in FIG. 2, creates a locked interference fit between proximal member 130 and distal member 140. First end 302 has a plurality of substantially similar grooves 326 and 328, which form an "L-shape" with surface 330 of end 302. Grooves 326 and 328 are provided to receive instrument 120 of fixation system 100, which is later described. In other non-limiting embodiments, other similar instruments may be provided to be received within grooves 326 and 328.

Distal member 140 further comprises a generally smooth portion 310 coupled to end 302. Portion 310 has a generally hexagonal shaped aperture 312, which opens into aperture 316 and which longitudinally traverses through portion 310 in direction 301. In other non-limiting embodiments, a star-shaped aperture, a square-shaped aperture, or any other shaped aperture may be utilized. Circular aperture 316 has a diameter 314 that is slightly larger than external diameter 224 of portion 216 and 206 of proximal screw member 130, with portions 216 and 206 being slidably received within aperture 316 of portion 310. Aperture 316 has a diameter that is smaller than diameter 226 of bulbous portion 202.

Portion 310 of distal member 140 terminates into a second generally cylindrical portion 318 which has a plurality of threads 324, which are circumferentially disposed on the external surface of portion 318. Portion 318 has an internal circular aperture 327 which is longitudinally coextensive with portion 318 in direction 301. Circular aperture 327 aligns with aperture 312 to form a continuous opening from end 302 to end 304.

Figure 4:
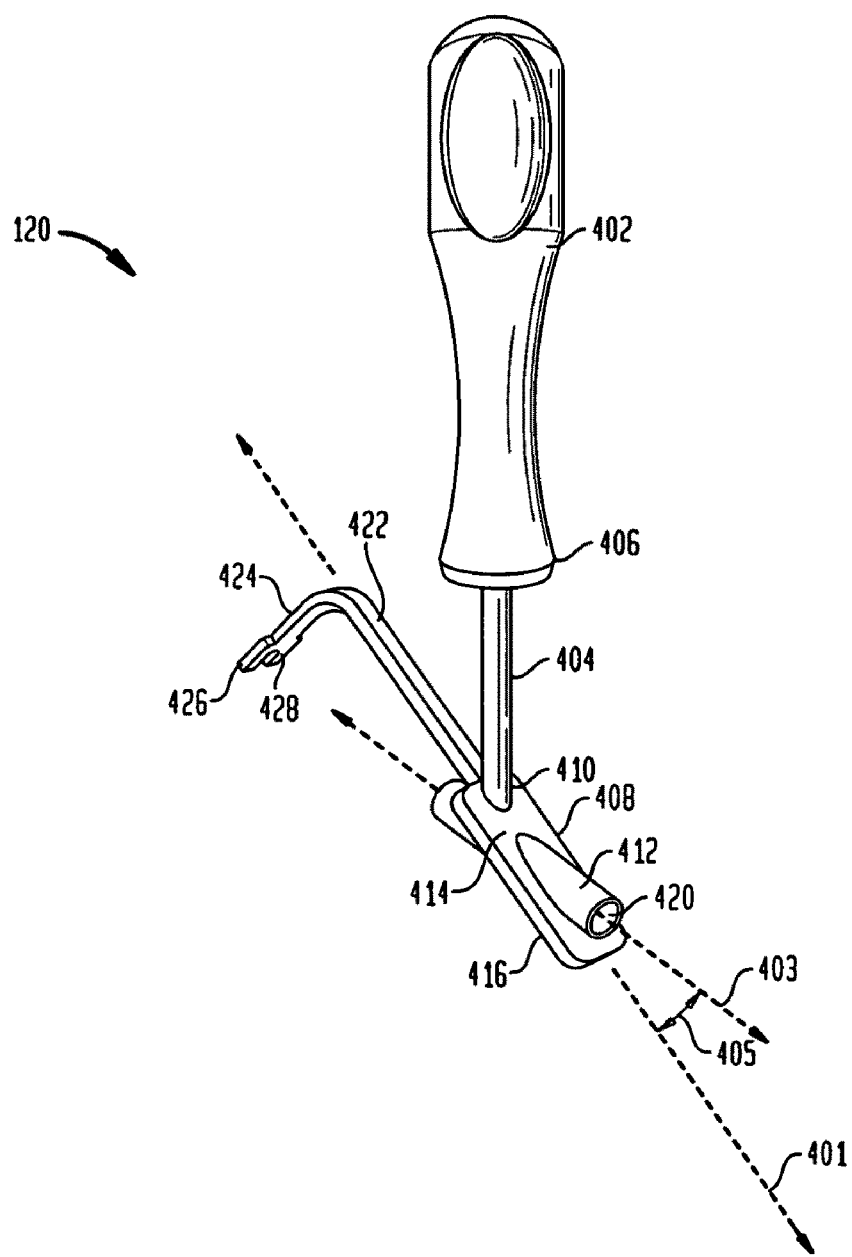
FIG. 4 is a perspective view of the instrument member used in the fixation system shown in FIG. 1 according to the preferred embodiment of the invention.

As shown in FIG. 4, instrument 120 is illustrated for coupling proximal screw member 130 to distal member 140. Particularly, instrument 120 includes a handle portion 402 coupled to a rod portion 404. Rod portion 404 emanates from handle portion 402 at end 406 and terminates into a rectangular planar portion 408 at end 410. Planar portion 408 is aligned along axis 401 and is fixably coupled to a generally cylindrical tubular portion 412 (i.e., an aiming device). Portion 412 traverses portion 408 from top surface 414 to bottom surface 416. Further, tubular portion 412 is aligned along dissimilar axis 403, forming an angle 405 with axis 401. Also, tubular portion 412 has a through aperture 420 that longitudinally traverses portion 412 along axis 403.

Planar portion 408 is coupled to planar portion 422, with portion 422 having a width slightly smaller than width of portion 408. Portion 422 terminates into a generally "U-shaped" portion 424 with portion 424 being orthogonal to portion 422. Further, portion 424 has a plurality of substantially similar sides 426 and 428 which are provided to be slidably coupled to grooves 326 and 328 of distal member 140.

In operation, sides 426 and 428 of instrument 120 are received in respective grooves 326 and 328 of distal member 140, of FIGS. 3A-3B, thereby slidably coupling distal member 140 to instrument 120. In this position, axis 303 of aperture 316 is aligned along substantially the same axis as axis 403 of instrument 120. Proximal screw member 130 is coupled to distal member 140 by slidably coupling portions 206 and 216 through aperture 420 of tubular portion 412. Tubular portion 412 guides proximal screw member 130 through internal aperture 420 and into aperture 316 on surface 322 and may also guide a Kirschner wire (K wire) or a drill. Proximal screw member 130, of FIG. 2, travels into bone as portions 216 and 206 travel further through aperture 316 at end 302 until bulbous portion 202 is restrained by surface 322 and end 302. Aperture 316, being tapered along axis 303, causes proximal screw member 130 to form an angle 150 with distal member 140, with proximal member 130 being aligned along an axis 303, which is substantially the same axis as axis 403 of tubular portion 412 of instrument 120.

Figure 5:
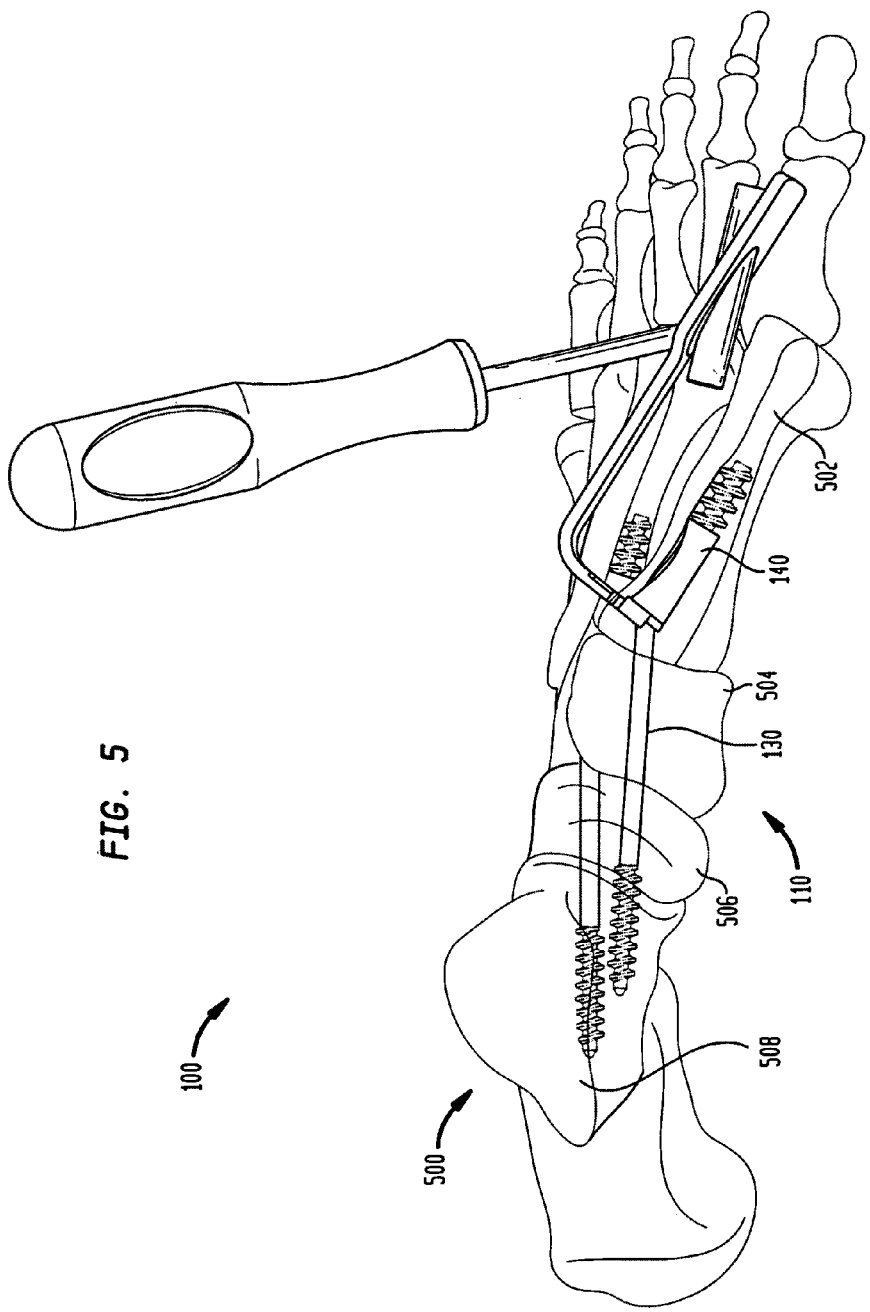
FIG. 5 is a perspective view of the assembled intramedullary fixation assembly inserted into the bones of a patient's foot according to the preferred embodiment of the invention.
Figure 6:
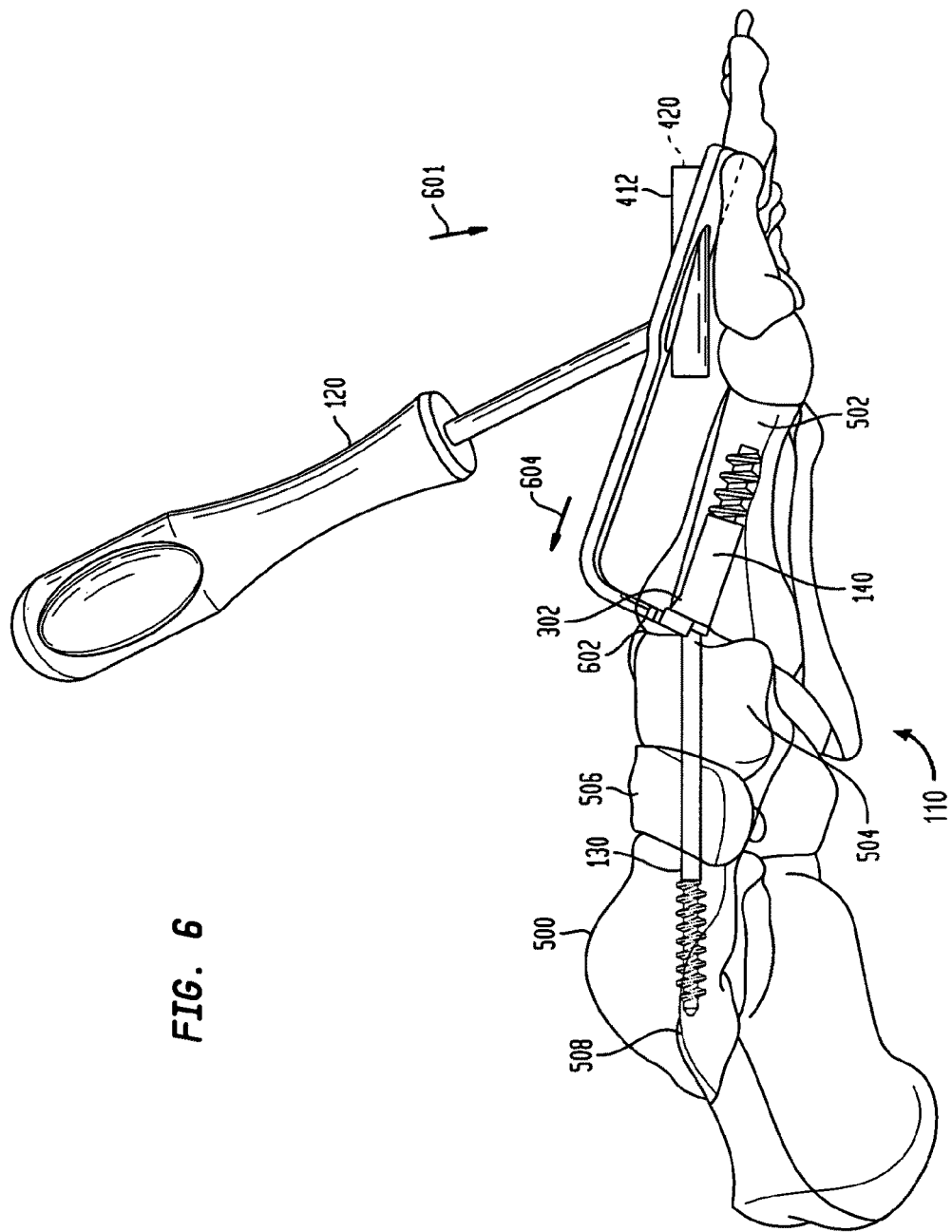
FIG. 6 is a side view of the assembled intramedullary fixation assembly shown in FIG. 5 according to the preferred embodiment of the invention.
Figure 7:
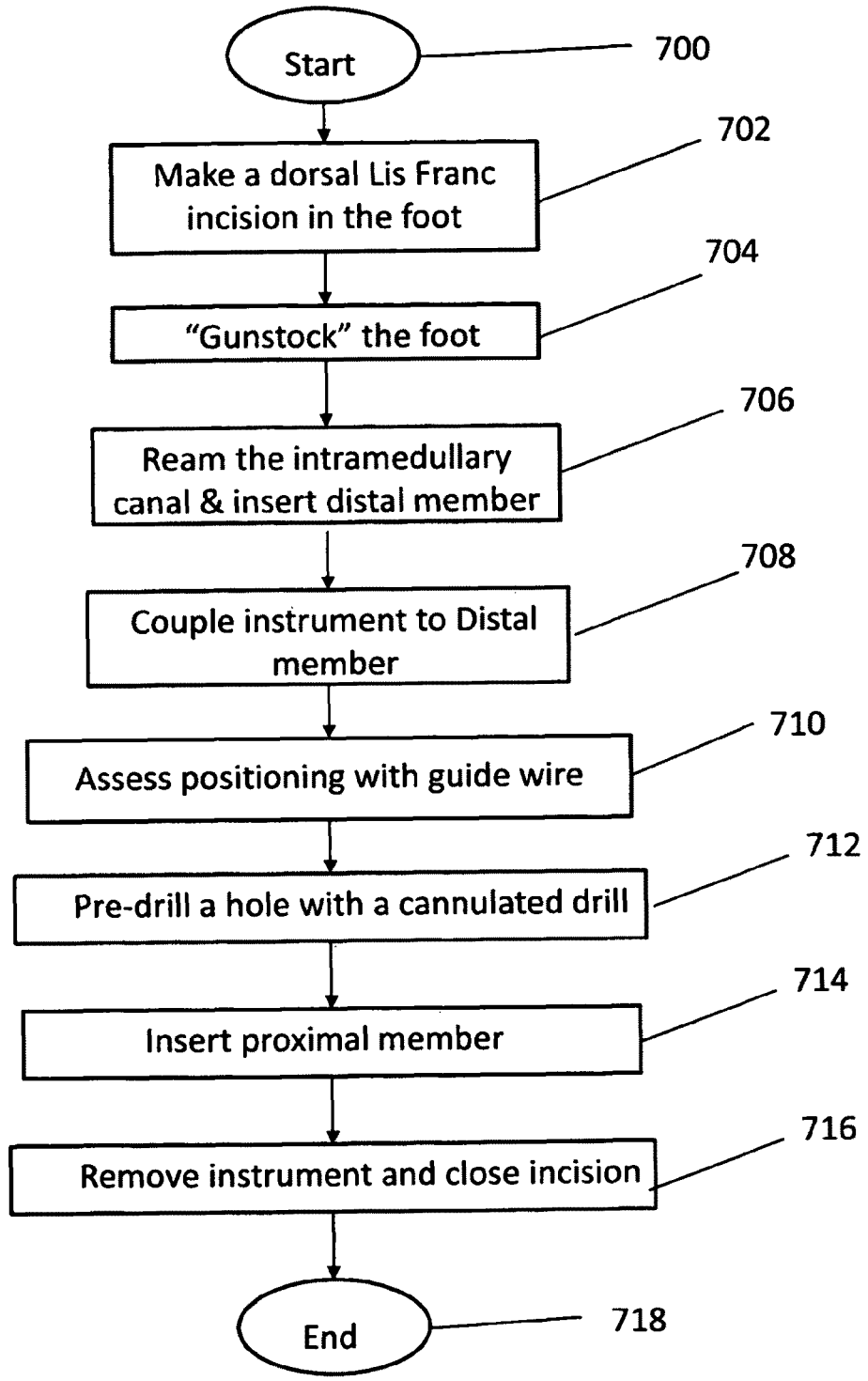
FIG. 7 is a flow chart illustrating the method of coupling the intramedullary fixation assembly shown in FIGS. 1-6 to tarsal and metatarsal bones in a patient's foot according to the preferred embodiment of the invention.

In operation, and as best shown in FIGS. 5, 6 and 7, the fixation system 100 utilizes the intramedullary fixation assembly 110 for treating and fixating the deteriorated and damaged or fractured bones in the human foot 500. This restores the arch in a human foot 500 by coupling the intramedullary fixation assembly 110 to the human foot 500 of a left leg. In one-non limiting example, and as shown in FIG. 5, the intramedullary assembly 110 is coupled to the medullary canals of the first metatarsal 502, medial cuneiform 504, navicular 506 and talus bone 508. Talus bone 508 makes up part of the ankle joint where the threaded portion 216 of the proximal screw member 130 of the intramedullary assembly 110 is threadably coupled. The medial cuneiform 504 and navicular 506 bones are most affected by Diabetic Charcot foot disorder that causes deterioration and collapse of the arch of the foot 500. It should be appreciated that the intramedullary assembly 110 may be used within each of the five rays, with a ray representing a line drawn from each metatarsal bone to the talus. The angulation in the smaller rays will be smaller than the two rays (i.e., a line from the first and second metatarsal bones to the talus bone). Also, the diameter of distal member 140 will decrease from the large ray to the small ray. In one non-limiting example, the angulation may be any angle greater than 90 degrees and less than 180 degrees. For example, the angle for the first ray may be 150-170 degrees and the angles for the other rays may be 160-175 degrees.

As shown in FIGS. 6 and 7, the intramedullary fixation assembly 110 may be utilized to reconstruct an arch in a mid-foot region of a human foot 500. As shown, the method starts in step 700 and proceeds to step 702, whereby a Dorsal Lis Franc incision (i.e., mid-foot incision) (not shown) is made in foot 500 in order to gain access to the joint. In step 704, the joint capsule is separated by "Gunstocking" foot 500 in direction 601 (i.e., the foot 500 is bent mid-foot) to expose the articular surface 602 and the articulating cartilage is removed. Next, in step 706, the intramedullary canal is reamed and the distal member 140 is inserted into the intramedullary. canal (not shown) of the metatarsal 502. In other non-limiting embodiments, the distal member 140 may be inserted by impaction, by press fit, by reaming a hole in the intramedullary canal (not shown) or substantially any other similar strategy or technique.

Next, in step 708, the instrument 120 is coupled to the distal member 140 by coupling sides 426 and 428 of instrument 120 to respective grooves 326 and 328. In step 710, initial positioning of the proximal member 130 is assessed with the use of a guide wire through portion 412 (i.e., aiming device). Next, in step 712, a countersink drill is inserted through portion 412 and the proximal cortex is penetrated. In this step, a cannulated drill or guide wire is used to pre-drill the hole through the joints selected for fusion. In step 714, the proximal screw member 130 is inserted over the guide wire and into the distal member 140. Particularly, the proximal member 130 is inserted through tubular portion 412 (i.e., aiming device), causing proximal member 130 to travel through internal longitudinal aperture 420, into distal member 140 and further into bones 504, 506 and 508 until rigid connection with the tapered aperture 316 is made, thereby compressing the joint. In one non-limiting embodiment, a locking element (not shown) such as a plate or a washer is coupled to end 302 of the intramedullary fixation assembly 110 to further secure proximal threaded member 130 to distal member 140. Next, in step 716 the instrument 120 is removed and the dorsal Lis Franc (i.e., mid-foot) incision is closed. The method ends in step 718.

It should be appreciated that a plurality of intramedullary fixation assemblies, such as intramedullary fixation assembly 110, may be inserted into any of the bones of a foot 500 such as, but not limited to the metatarsal, cuneiform, calcaneus, cuboid, talus and navicular bones, in order to restore the natural anatomical shape of the arch of the foot 500. Thus, the fixation system 100, in one non-limiting embodiment, is utilized to couple the intramedullary fixation assembly 110 to the foot 500, which causes the metatarsal 504, medial cuneiform 504, navicular 506 and talus 508 bones to be aligned to the proper anatomical shape of an arch when assembled within foot 500. It should be appreciated that the intramedullary fixation assembly 110 is delivered through a dorsal midfoot incision, thereby reducing the disruption to the plantar tissues and/or the metatarsal heads while at the same time minimizing the tension on the skin. This allows for improved wound closure, reduced operating room time, reduction in the number of incisions required and reduction in the total length of incisions. It should also be appreciated that in other non-limiting embodiments, the intramedullary assembly 110 may be utilized with graft material (i.e., autograft, allograft or other biologic agent).

Figure 8:
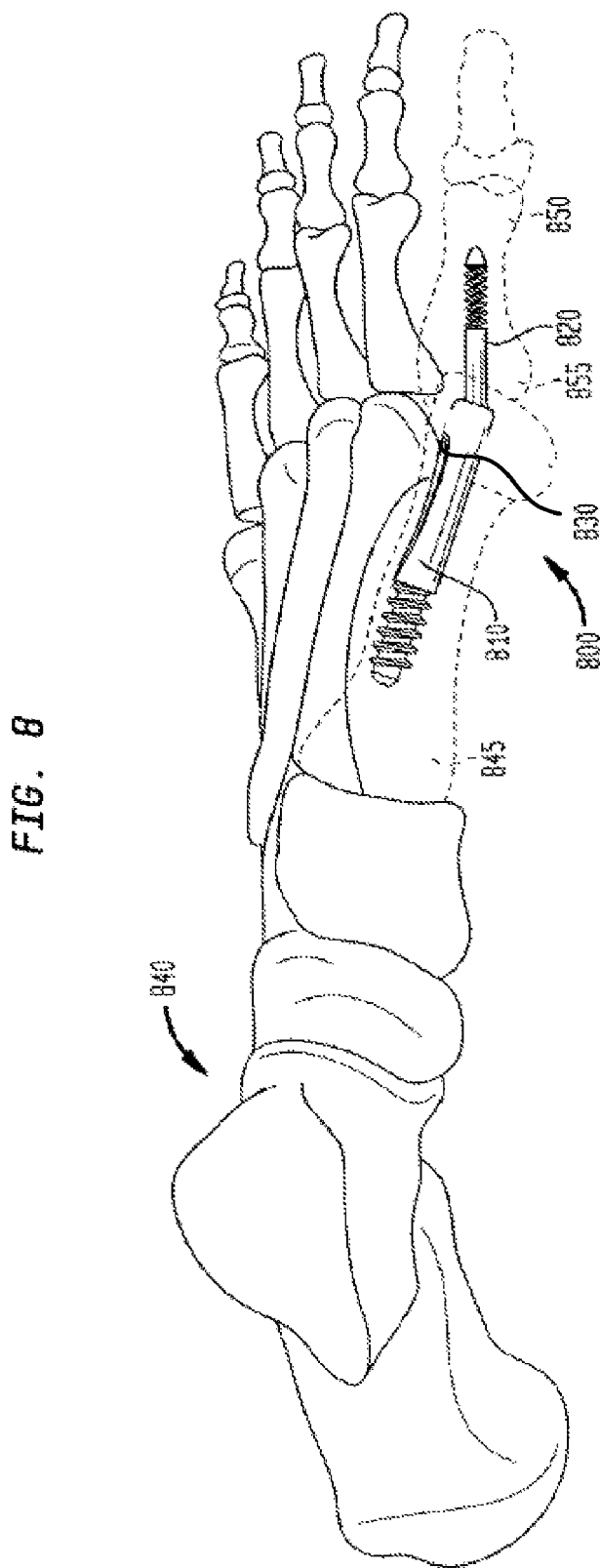
FIG. 8 is a perspective view of an assembled intramedullary fixation assembly inserted into the metatarsal and trapezial bones of a patient's foot according to an alternate embodiment of the invention.

In an alternate embodiment, as shown in FIG. 8, an intramedullary fixation assembly 800 may comprise three interconnected members for the internal fixation of the first metatarsal 845 to the first proximal phalange 850 in the human foot 840 or any other appropriate use for the internal fixation of the other bones in the human foot 840. The interconnected members of the intramedullary fixation assembly 800 may be inserted into the medullary canals of the first metatarsal 845 and the first proximal phalange 850 in order to restore the angle in the toes of a human foot 840. Particularly, the intramedullary fixation assembly 800 may comprise a metatarsal implant member 810, a phalangeal implant member 820 and an optional locking set screw 830.

Figure 9:
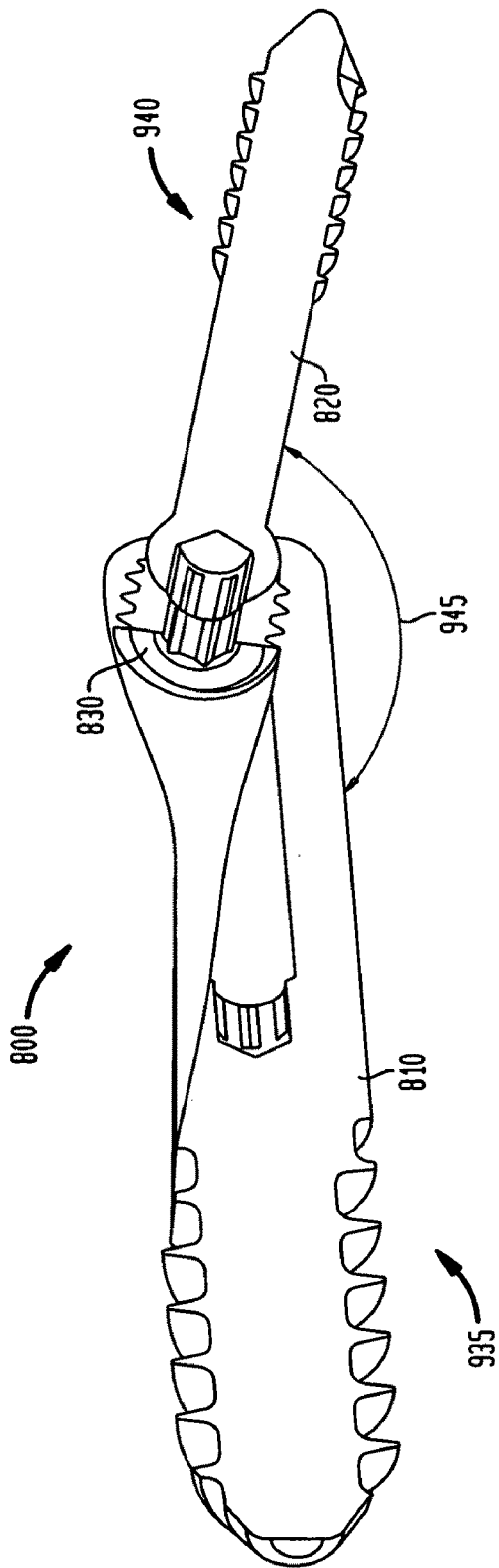
FIG. 9 is a perspective cross-sectional view of the intramedullary fixation assembly according to the alternate embodiment of the invention.

As shown in FIG. 9, the intramedullary fixation assembly 800 comprises the metatarsal implant member 810, which is provided on the proximal end 935 of the intramedullary fixation assembly 800, the phalangeal implant member 820 provided on the distal end 940 and the optional locking set screw 830 provided to threadably couple to the metatarsal implant member 810, thereby pressure coupling the metatarsal implant member 810 to the phalangeal implant member 820. Optional locking set screw 830 thereby locks the metatarsal implant member 810 to the phalangeal implant member 820 and allows for incremental adjustment of the position of phalangeal implant member 820 within the metatarsal implant member 810 as will be shown and described.

In its implanted position, metatarsal implant member 810 is at a fixed angle 945 with phalangeal implant member 820 and this angle 945 may be adjusted in order to set the angle for restoration. It should be appreciated that in one non-limiting embodiment, intramedullary fixation assembly 800 may be made from a Titanium material, although, in other non-limiting embodiments, intramedullary fixation assembly 800 may be made from SST, PEEK, NiTi, Cobalt chrome or other similar types of materials.

Figure 10A:
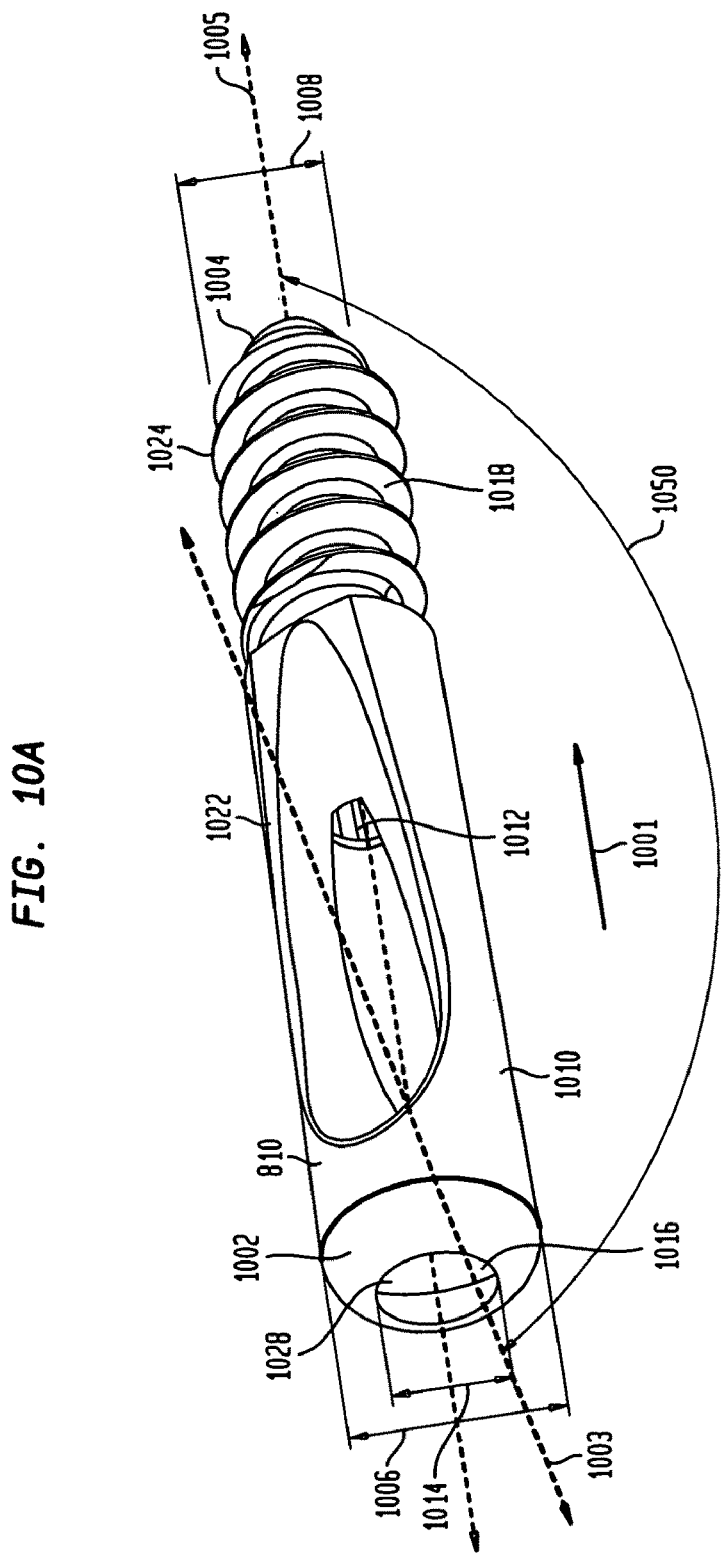
FIG. 10A is a perspective view of a metatarsal implant member used in the intramedullary fixation assembly shown in FIG. 8 according to the alternate embodiment of the invention.
Figure 10B:
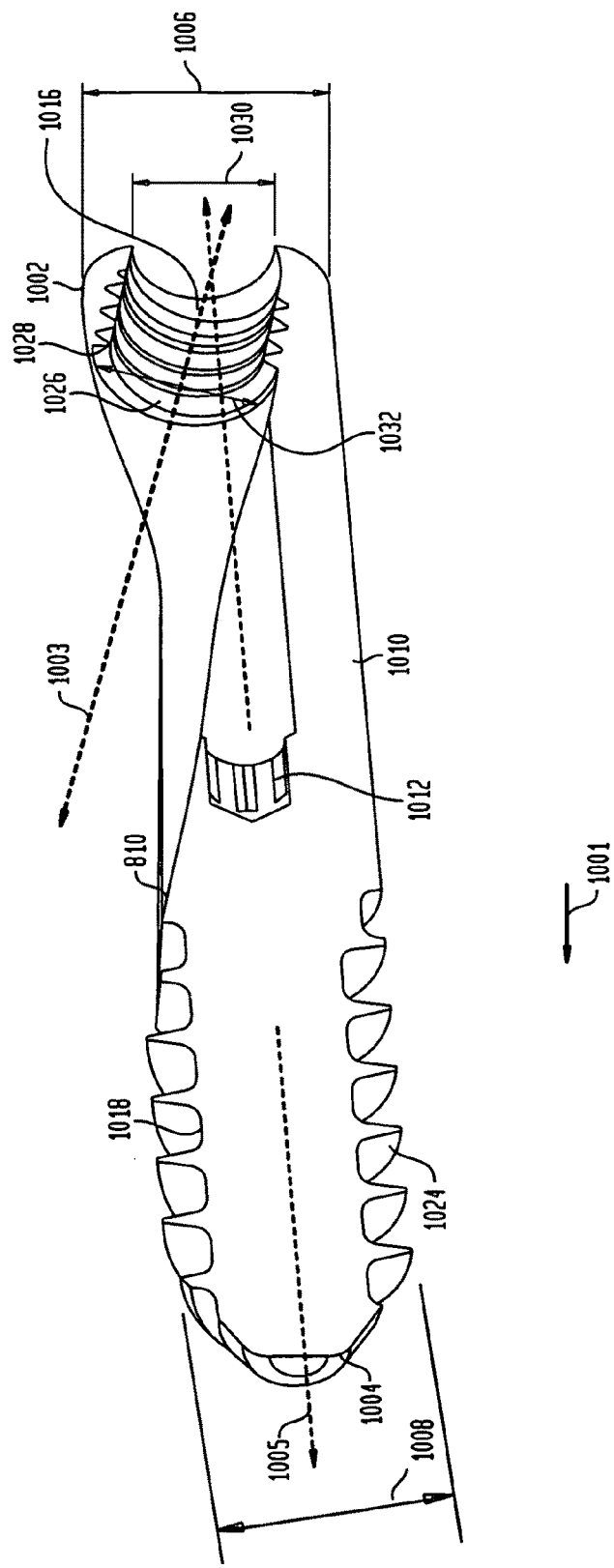
FIG. 10B is a perspective cross-sectional view of the metatarsal implant member used in the intramedullary fixation assembly shown in FIG. 10A according to the alternate embodiment of the invention.

As shown in FIGS. 10A-10B, metatarsal implant member 810 of the embodiment is generally tubular in shape and tapers from a first end 1002 to a second end 1004 (i.e. end 1002 has a diameter 1006 that is slightly larger than diameter 1008 of end 1004). However, in another non-limiting embodiment, metatarsal implant member 810 has a constant width from first end 1002 to second end 1004. Further, first end 1002 is generally semi-spherical in shape and has an internal circular aperture 1016, which traverses end 1002 along direction 1001 (i.e. end 1002 is generally "donut" shaped). Additionally, circular aperture 1016 is aligned along axis 1003, which is offset from horizontal axis 1005 at an angle 1050. Angle 1050 causes circular aperture 1016 to emanate from surface 1022, such that circular-aperture 1016 on cylindrical portion 1010 is generally tapered with the diameter 1030 being slightly smaller than diameter 1032.

It should be appreciated that angle 1050 initially determines the angle for restoration, as shown in FIG. 10A. Angle 1050 may be any angle greater than 90 degrees and less than 180 degrees. Circular aperture 1016 also includes a plurality of substantially similar threads 1028 that are provided on interior surface 1026 of metatarsal implant member 810. The plurality of substantially similar threads 1028 when combined with head portion 1105 of phalangeal implant member 820, shown in FIG. 11, creates a locked interference fit between metatarsal implant member 810 and phalangeal implant member 820. Circular aperture 1016 has a diameter 1014 that is provided to receive head portion 1105 of phalangeal implant member 820, which will be shown in FIG. 11.

Also, metatarsal implant member 810 further comprises a generally smooth portion 1010 coupled to end 1002. Portion 1010 has a generally hexagonal shaped aperture 1012 aligned along axis 1005.

In other non-limiting embodiments, a star-shaped aperture, a square-shaped aperture, or any other shaped aperture may be utilized. Aperture 1012 emanates from circular aperture 1016, traverses through portion 1010 in direction 1001 and terminates into a generally cylindrical portion 1018. In other non-limiting embodiments, aperture 1012 is longitudinally coextensive with portion 1018 in direction 1001 and emanates from second end 1004. In this manner, a continuous opening from end 1002 to end 1004 may be formed to receive a Kirschner wire (K wire) or a drill.

Further, portion 1018 has a plurality of substantially similar circumferential threads, such as threads 1024, which are circumferentially disposed on the external surface of portion 1018. It should be appreciated that plurality of circumferential threads, such as threads 1024, are provided so that rotating metatarsal implant member 810 causes the plurality of circumferential threads 1024 to grip or catch the medullary canal of first metatarsal 845 (shown in FIG. 8) causing metatarsal implant member 810 to travel into the first metatarsal 845. It should be appreciated that metatarsal implant member 810 may be utilized in any metatarsal for restoration of the angle in the human foot. It should also be appreciated that the metatarsal implant member may be utilized for fusion-of other joints in the human body.

Figure 11:
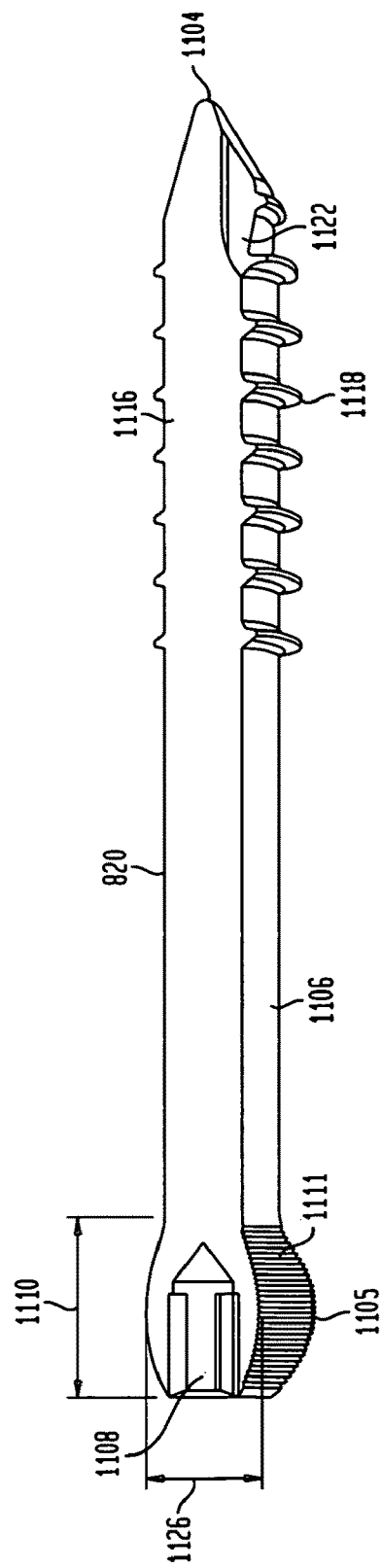
FIG. 11 is a perspective cross-sectional view of a phalangeal implant member used in the intramedullary fixation assembly shown in FIG. 8 according to the alternate embodiment of the invention.

As shown in FIG. 11, phalangeal implant member 820 is generally cylindrical in shape, has a generally solid body and extends from a spherical head portion 1105 to tapered end 1104. Spherical head portion 1105 is generally spherical in shape and has a generally hexagonal torque transmitting aperture 1108 traversing length 1110 of head portion 1105. In other non-limiting embodiments, a star-shaped aperture, a square-shaped aperture, or any other shaped aperture of any length may be utilized without departing from the scope of the invention. Torque transmitting aperture 1108 is utilized to transmit a torque from head portion 1105 to tapered end 1104 when head portion 1105 is rotated. The largest diameter 1126 of head portion 1105 is slightly larger than diameter 1032 of circular aperture 1016 on metatarsal implant member 810, which was shown previously in FIGS. 10A-B.

Head portion 1105 further has a plurality of generally flat edges 1111 (i.e., head portion 1105 has a plurality of step-like protrusions) which are provided to engage circular aperture 1016. The flat edges 1111 allow for the phalangeal implant member 820 to be coupled at a plurality of angles to metatarsal implant member 810. Each of the plurality of edges 1111 allows for a unique angle in a locked interference fit to be created by head portion 1105 within circular aperture 1016, shown in FIGS. 10A-B, as head portion 1105 of phalangeal implant member 820 is positioned within circular aperture 1016 of metatarsal implant member 810, which will be shown and described below Further, phalangeal implant member 820 has a first smooth exterior portion 1106 extending from head portion 1105. Portion 1106 is generally cylindrical and terminates into a second generally cylindrical portion 1116, with exterior portion 1106 and cylindrical 1116 having a uniform diameter. Furthermore, cylindrical portion 1116 has a plurality of circular threads, such as threads 1118, which are circumferentially disposed on the external surface of portion 1116. Cylindrical portion 1116 may also be provided with a self-tapping leading edge 1122 to provide portion 1116 with the ability to remove bone material during insertion of the phalangeal implant member 820 into bone or other matter. It should be appreciated that the length of the phalangeal implant member 820 may be selected of varying lengths to allow a surgeon to fuse different joints (not shown). In other non-limiting embodiments, the phalangeal implant member 820 may have a continuous opening (i.e., a cannula) from torque transmitting aperture 1108 to tapered end 1104. The continuous opening or cannula may be provided to interact with a guide wire (not shown), such as a Kirschner wire, by receiving the guide wire within the continuous opening thereby positioning and locating the phalangeal implant 820.

Figure 12:
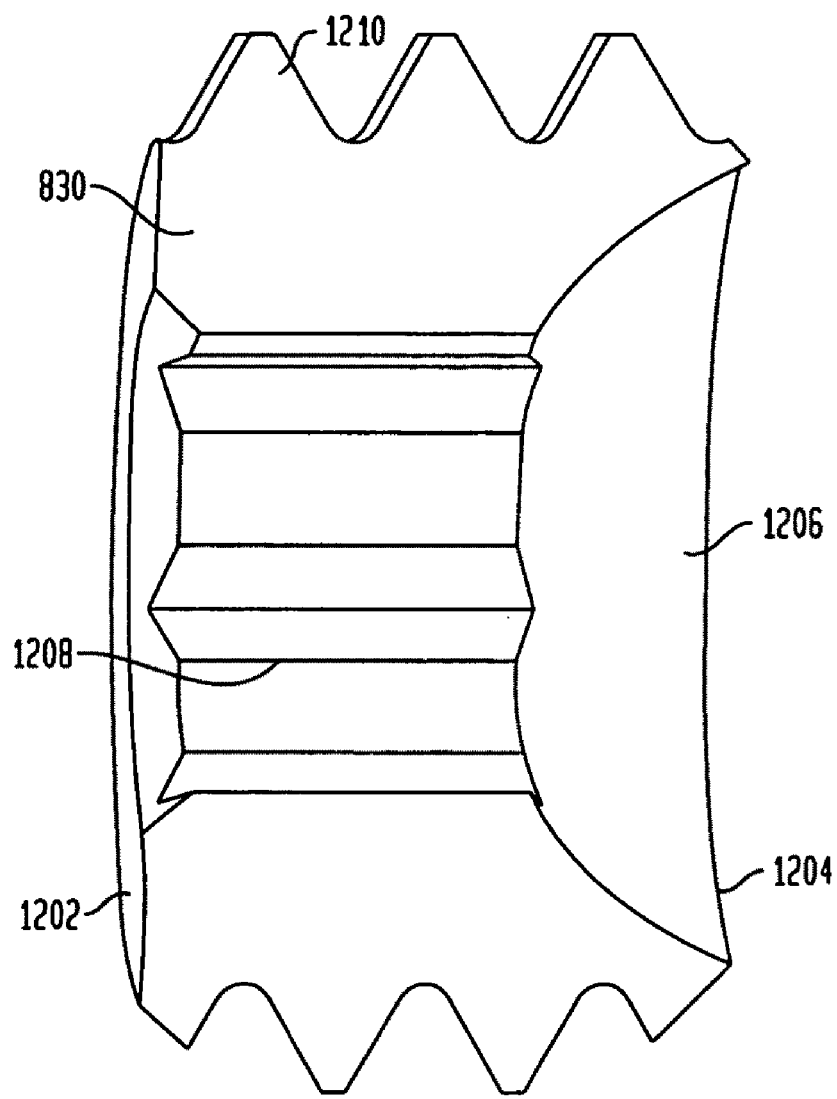
FIG. 12 is a perspective cross-sectional view of a locking set screw used in the intramedullary fixation assembly shown in FIG. 8 according to the alternate embodiment of the invention.

As shown in FIG. 12, intramedullary fixation assembly 800 may comprise an optional locking set screw 830 to couple the metatarsal implant member 810 to the phalangeal implant member 820. Locking set screw 830 is generally tubular in shape and extends from open first end 1202 to an-open second end 1204. First end 1202 has a generally flat surface while second end 1204 has a semi-spherical groove 1206. The semi-spherical groove 1206 is provided to receive head portion 1105 of the phalangeal implant member 820 in an assembled intramedullary fixation assembly 800. Further, locking set screw 830 has a generally hexagonal torque-transmitting aperture 1208 that traverses from first end 1202 to second end 1204. In other non-limiting embodiments, a star-shaped aperture, a square-shaped aperture, or any other shaped aperture of any length may be utilized without departing from the scope of the invention.

Torque transmitting aperture 1208 is utilized to receive a torque shaped tool in order to rotate and couple locking set screw 830 to first metatarsal implant member 810 (not shown). Locking set screw 830 is also provided with a plurality of substantially similar circumferential threads 1210 in order to engage the plurality of threads 1028 on the interior surface 1026 of the metatarsal implant member 810 (shown in FIGS. 10A and 10B) and threadably couple (i.e., mechanically couple) the locking set screw 830 to the metatarsal implant member 810, thereby preventing the phalangeal implant member 820 from backing out of circular aperture 1016 on metatarsal implant member 810 and losing compression.

Figure 13:
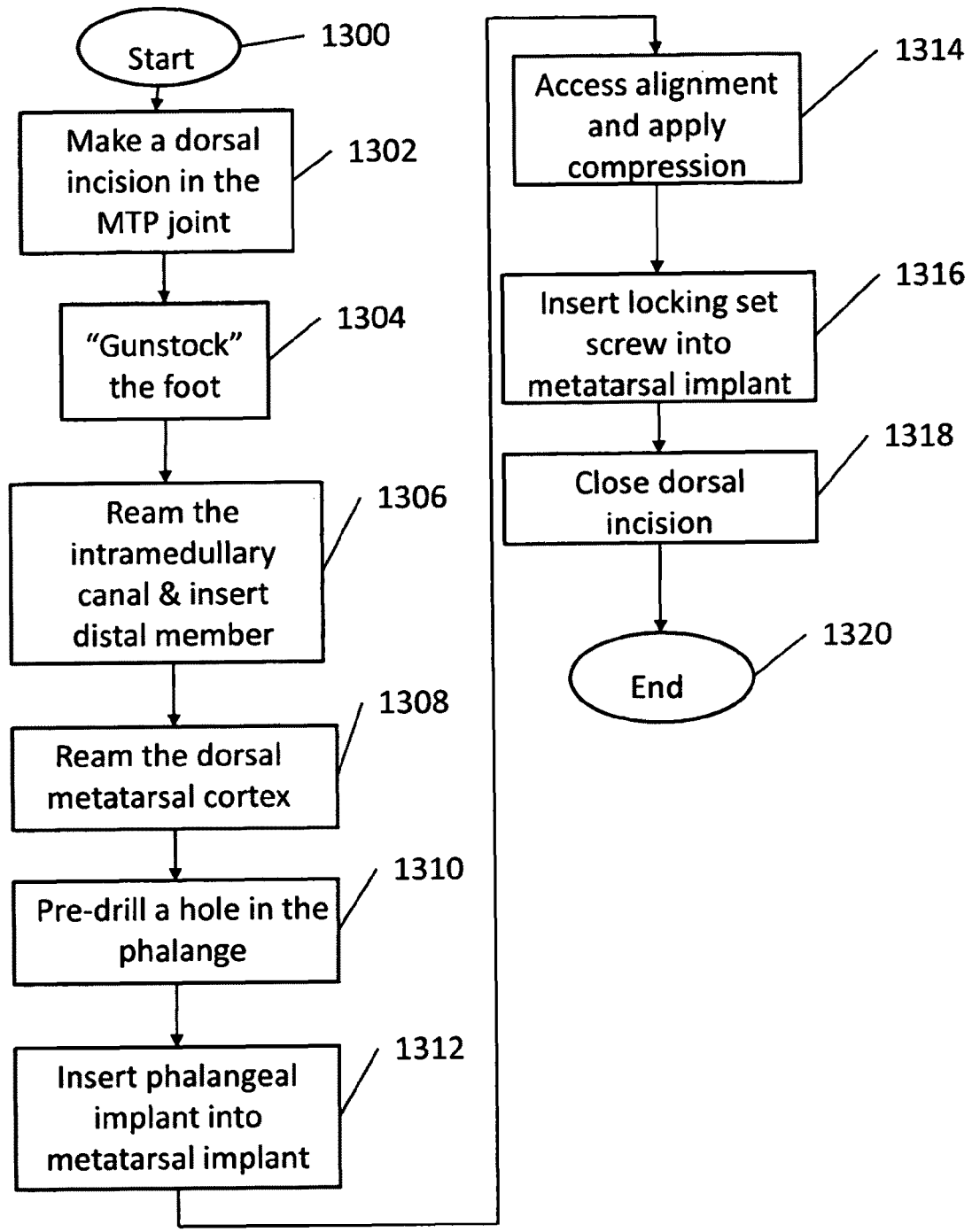
FIG. 13 is a flow chart illustrating the method of coupling the intramedullary fixation assembly shown in FIGS. 8-12 to metatarsal and phalangeal bones in a patient's foot according to the alternate embodiment of the invention.

In operation, and as shown in FIGS. 8 and 13, the intramedullary fixation assembly 800 may be utilized to reconstruct an arch and/or angle in a metatarsal phalangeal joint of a human foot 840. As shown, the method starts in step 1300 and proceeds to step 1302, whereby a dorsal incision is made in the metatarsal phalangeal (MTP) joint 855 of foot 840 in order to gain access to the MTP joint 855. In step 1304, the joint capsule is separated by "Gunstocking" foot 840 (i.e., the foot 840 is bent at MTP joint 855) to expose the articular surfaces of the metatarsal 845 and first proximal phalange 850. The articulating cartilage is removed by denuding the cartilage in the MTP joint 855. Next, in step 1306, the intramedullary canal of the metatarsal 845 is reamed by drilling the metatarsal intramedullary canal and the metatarsal implant member 810 is inserted. The cylindrical portion 1018 of the metatarsal implant member 810 is inserted first into the intramedullary canal (of the metatarsal 845 to a predetermined depth until end 1002 is oriented at the opening of the MTP joint 855. In other non-limiting embodiments, the metatarsal implant member 810 may be inserted by impaction, by press fit, by reaming a hole in the intramedullary canal (not shown) or any other similar strategy or technique.

Next, in step 1308, the dorsal metatarsal cortex (not shown) is drilled and reamed to allow access to metatarsal implant member 810 from an anterior grade access. In step 1310, a cannulated drill or guide wire is used to pre-drill a pilot hole through the articular surface of the phalange 850. In step 1312, the phalangeal implant member 820 is inserted into the metatarsal implant member 810 and into the pre-drilled pilot hole by inserting the tapered end 1104 (shown in FIG. 11) into the circular aperture 1016 (shown in FIG. 10A-B) at surface 1022 and until the tapered end 1104 emanates from circular aperture 1016. Further, the phalangeal implant member 820 is inserted into the phalange 850 (shown in FIG. 8). Next in step. 1314, the phalangeal implant member 820 is aligned and angle 845 (shown in FIG. 9) is formed and compression is applied to the intramedullary fixation assembly 800 by rotating the phalangeal implant member 820. The phalangeal implant member 820 is fixed at angle 845 (shown in FIG. 9). In optional step 1316, the locking set screw 830 is inserted into metatarsal implant member 810 to lock angle 845 (shown in FIG. 9) in place. Next, in step 1318, the dorsal incision is closed. The method ends in step 1320.

Figure 14:
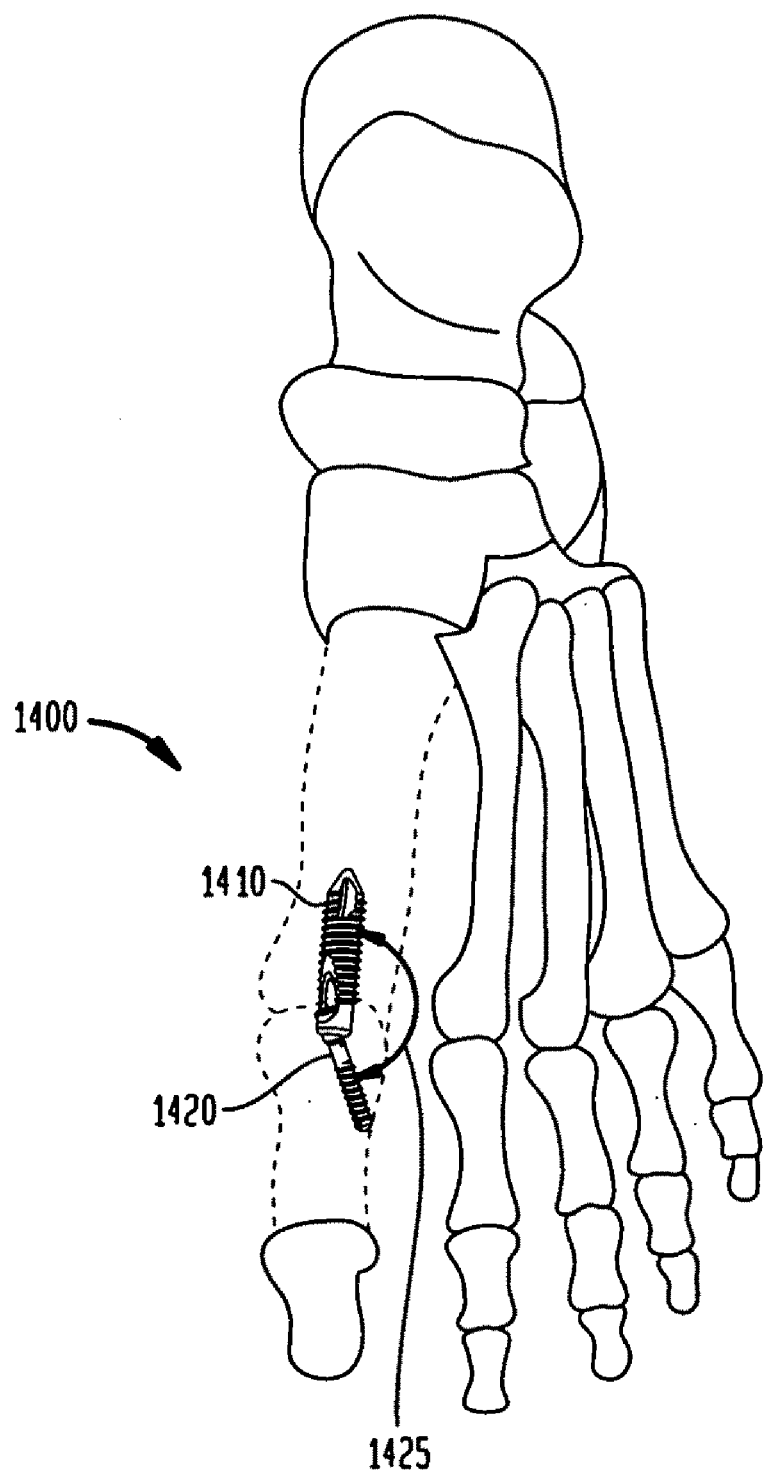
FIG. 14 is a perspective cross-sectional view of an intramedullary fixation assembly according to the alternate embodiment of the invention.
Figure 15:
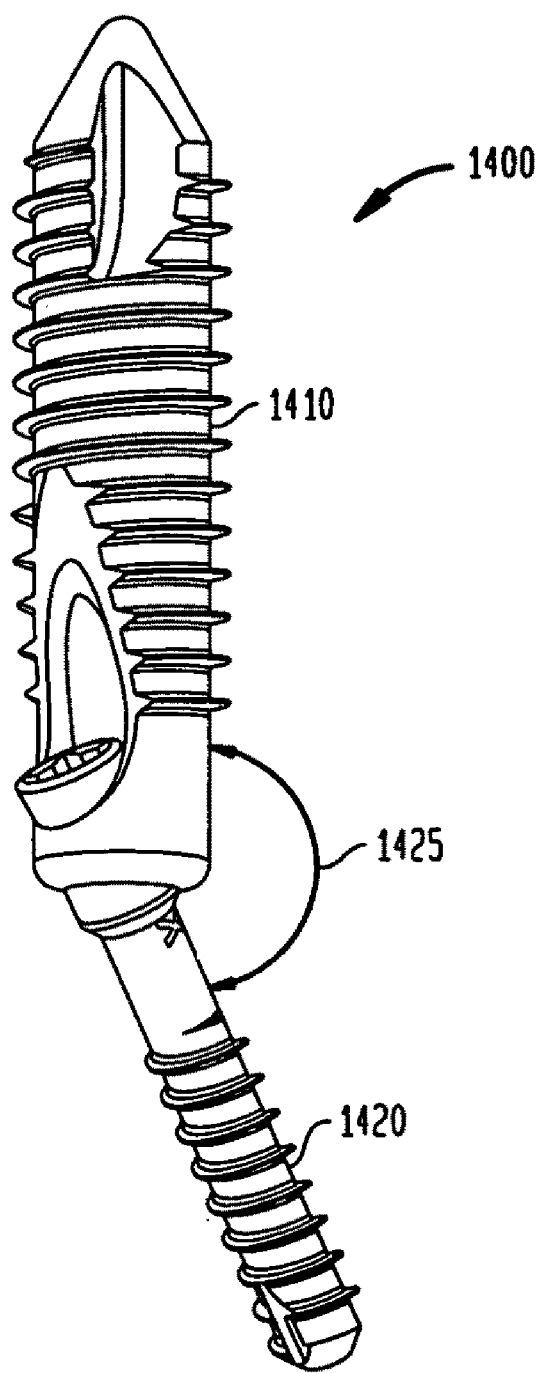
FIG. 15 is a perspective view of the intramedullary fixation assembly shown in FIG. 14 according to the alternate embodiment of the invention.

In an alternate embodiment, as shown in FIGS. 14 and 15, intramedullary fixation assembly 1400 is provided so that metatarsal implant member 1410 resides at a constant and fixed angle 1425 with phalangeal implant member 1420. The fixed angle 1425 may be any angle greater than 90 degrees and less than 180 degrees and may be selected by, in one example, a surgeon to provide for the internal fixation of the bones in the human foot.

Figure 16:
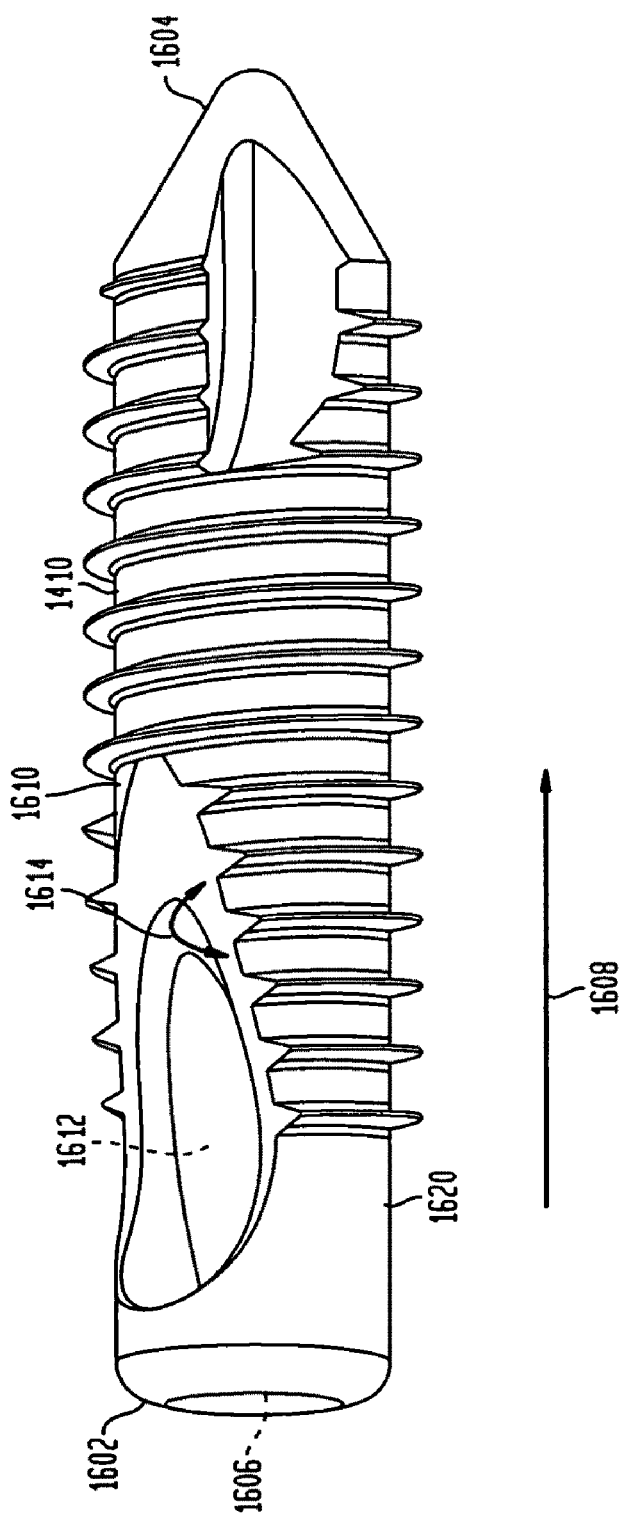
FIG. 16 is a perspective view of a metatarsal implant member used in the intramedullary fixation assembly shown in FIGS. 14-15 according to the alternate embodiment of the invention.

The metatarsal implant member 1410, shown in FIG. 16, is substantially similar to the distal member 140 shown and described in a previous embodiment in FIGS. 3A and 3B, and is generally tubular in shape and tapers from a first end 1602 to a second end 1604 (i.e. end 1602 has a diameter that is slightly larger than diameter of end 1604). However, in another non-limiting embodiment, metatarsal implant member 1410 has a constant width from first end 1602 to second end 1604. Further, first end 1602 has an internal circular aperture 1606 partially traversing metatarsal implant member 1410 along direction 301. Additionally, metatarsal implant member 1410 has a longitudinal aperture 1612 emanating from surface 1610, such that aperture 1612 forms a slope 1614 from in portion 1620. Slope 1614 determines the angle for restoration of the bones in a foot when phalangeal implant member 1420 (not shown) is coupled to metatarsal implant member 1410 and locks the phalangeal implant member at the fixed angle.

Figure 17:
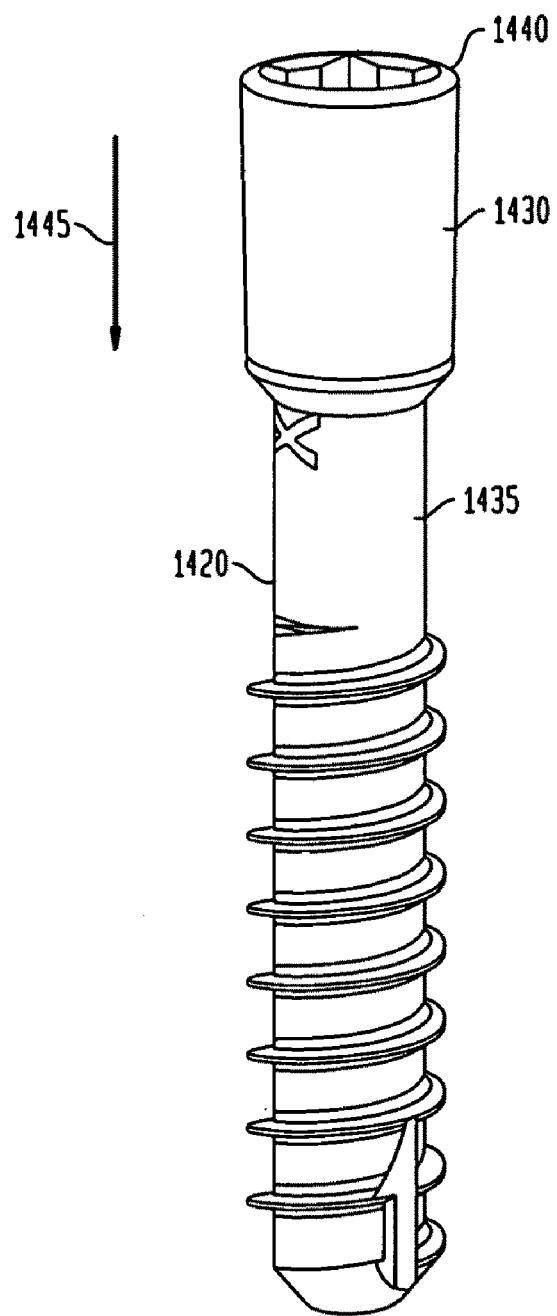
FIG. 17 is a perspective view of a phalangeal implant member used in the intramedullary fixation assembly shown in FIGS. 14-15 according to the alternate embodiment of the invention.

Also, the phalangeal implant member 1420, shown in FIG. 17, is substantially similar to the proximal screw member 130 that was shown in a previous embodiment, however, phalangeal implant member 1420 includes bulbous portion 1430 having a constant diameter. In other non-limiting embodiments, bulbous portion 1430 may include a morse taper the diameter decreases from end 1440 in direction 1445). The bulbous portion 1430 is provided to be received inside aperture 1606 so that phalangeal implant member 1420 resides at a fixed angle with respect to metatarsal implant member 1410.

It should be appreciated that a plurality of intramedullary fixation assemblies, such as intramedullary fixation assembly 800, may be inserted into any of the metatarsal and phalangeal bones of a foot 840 in order to restore the natural anatomical shape of the foot 840. It should also be appreciated that the intramedullary fixation assembly 800 is delivered through a dorsal incision, thereby reducing the disruption to the plantar tissues and/or the metatarsal heads while at the same time minimizing the tension on the skin. This allows for improved wound closure, reduced operating room time, reduction in the number of incisions required and reduction in the total length of incisions. It should also be appreciated that the intramedullary fixation assembly 800 may also be utilized to restore any of the other bones in the human body. It should also be appreciated that in other non-limiting embodiments, the intramedullary assembly 800 may be utilized with graft material (i.e., autograft, allograft or other biologic agent).

Figure 18:
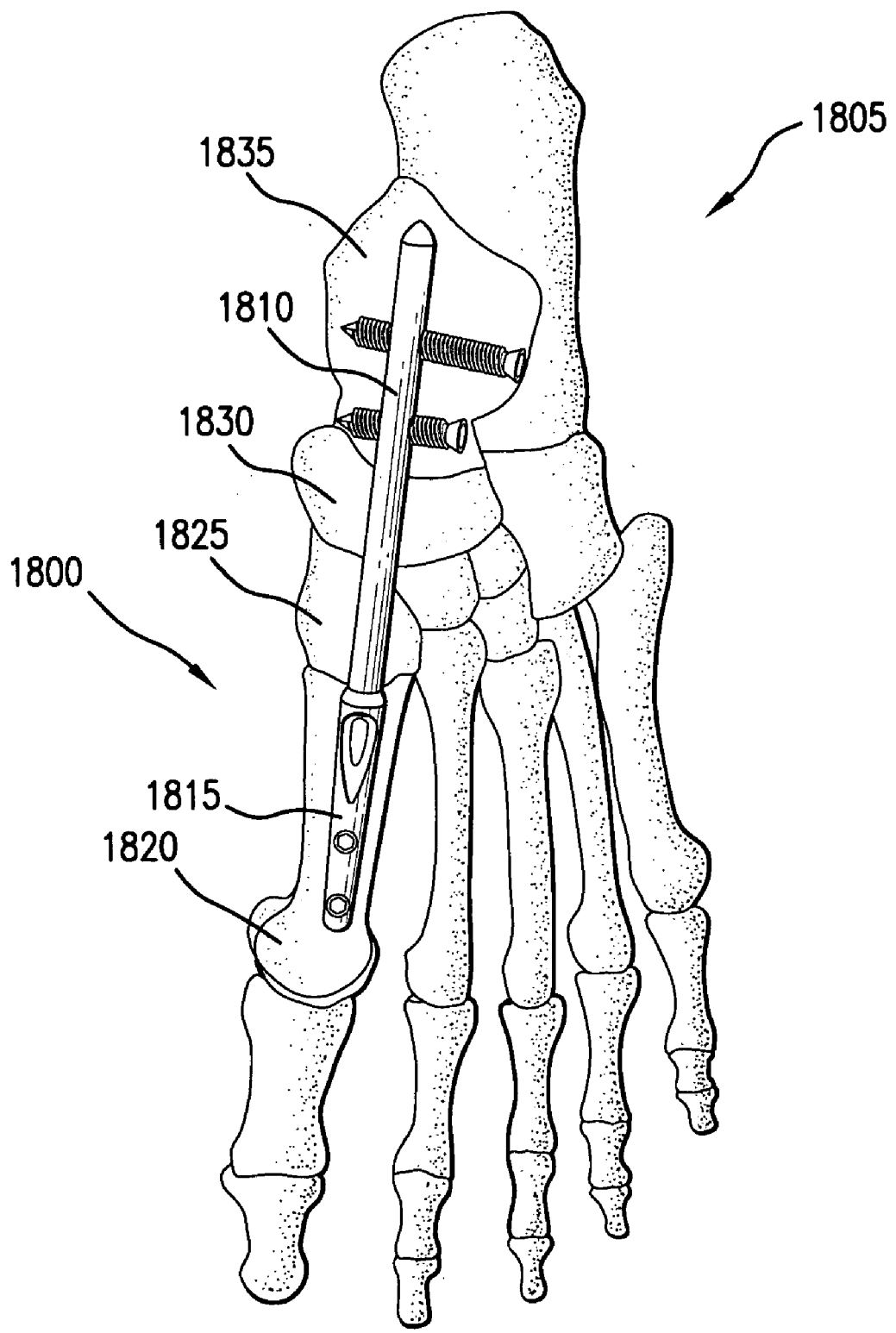
FIG. 18 is a perspective view of the assembled intramedullary fixation assembly inserted into the bones of a patient's foot according to an alternate embodiment of the invention.

In an alternate embodiment, as shown in FIG. 18, an intramedullary fixation assembly 1800 comprises a proximal member 1810 (or "beam") coupled to a distal member 1815 for the internal fusion of the bones of the human foot 1805, such as, for example, the first metatarsal bone 1820, the medial cuneiform bone 1825, the navicular bone 1830, and the talus bone 1835. In other non-limiting embodiments, the intramedullary fixation assembly 1800 may be utilized for any other appropriate use for the internal fixation of the other bones. As shown, the interconnected members of the intramedullary fixation assembly 1800, in one non-limiting example, may be inserted into the medullary canals of the first metatarsal bone 1820, the medial cuneiform bone 1825, the navicular bone 1830, and the talus bone 1835 in order to restore the arch in the human foot 1805. It should be appreciated that the intramedullary fixation assembly 1800 may be used within each of the five rays, with a ray representing a line drawn from each metatarsal bone to the talus bone 1835. Also, the fourth or fifth rays may go into the Calcaneus bone.

Figure 19:
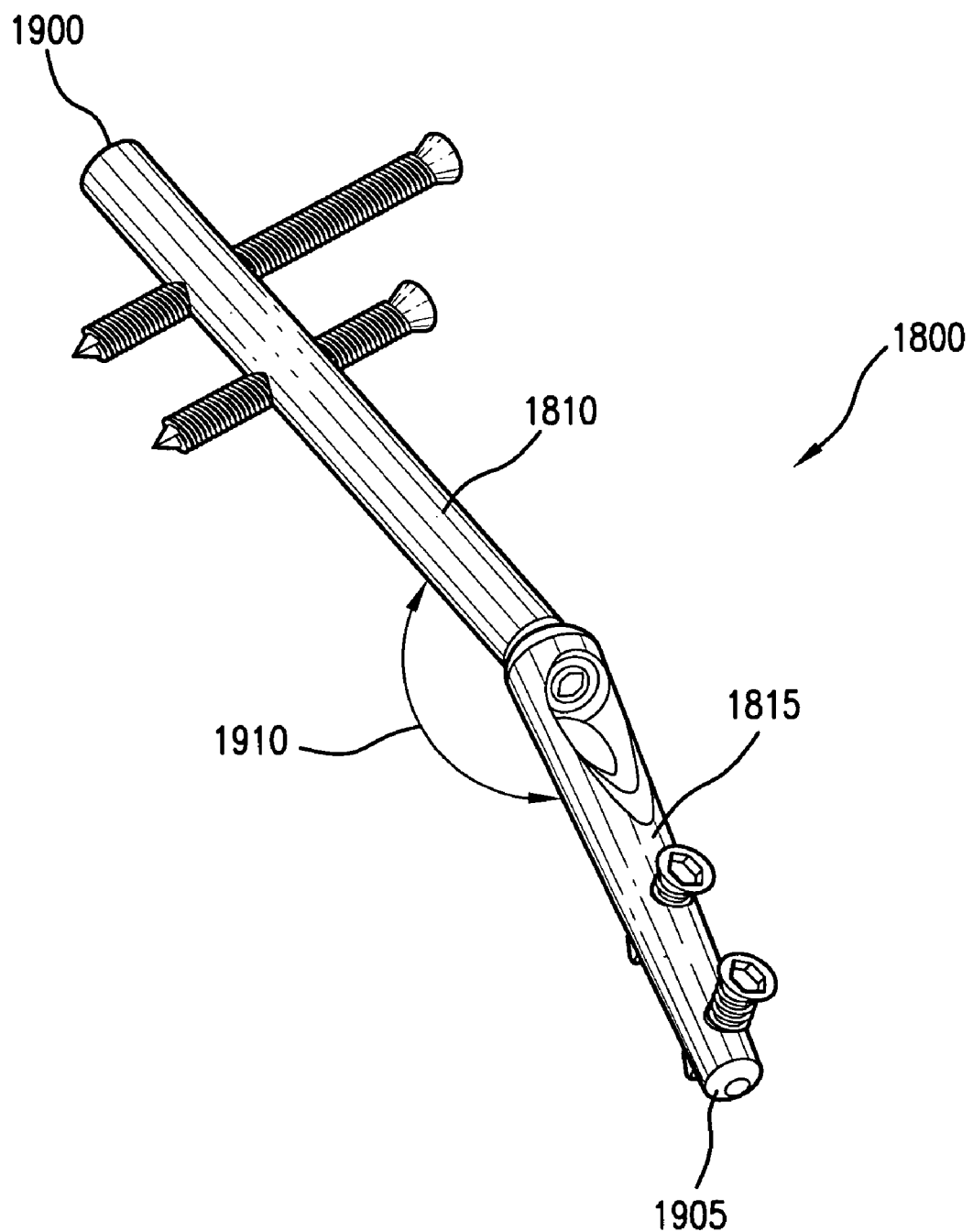
FIG. 19 is a perspective view of the intramedullary fixation assembly shown in FIG. 18 according to the alternate embodiment of the invention.

Also as shown in FIG. 19, the intramedullary fixation assembly 1800 includes the proximal member 1810 located on the proximal end 1900 of the intramedullary fixation assembly 1800 and the distal member 1815 located on the distal end 1905 of the intramedullary fixation assembly 1800.

The angular position of the proximal member 1810 may be incrementally adjusted in relation to the distal member 1815, thereby allowing for positioning the intramedullary fixation assembly 1800 at various angles of fixation. In its implanted position, proximal member 1810 is at a fixed angle 1910 with distal member 1815, with angle 1910 defining the angle for arch restoration. It should be appreciated that in one non-limiting embodiment, intramedullary fixation assembly 1800 may be made from a Titanium material, although, in other non-limiting embodiments, intramedullary fixation assembly 1800 may be made from SST, PEEK, NiTi, Cobalt chrome or other similar types of materials.

Figure 20:
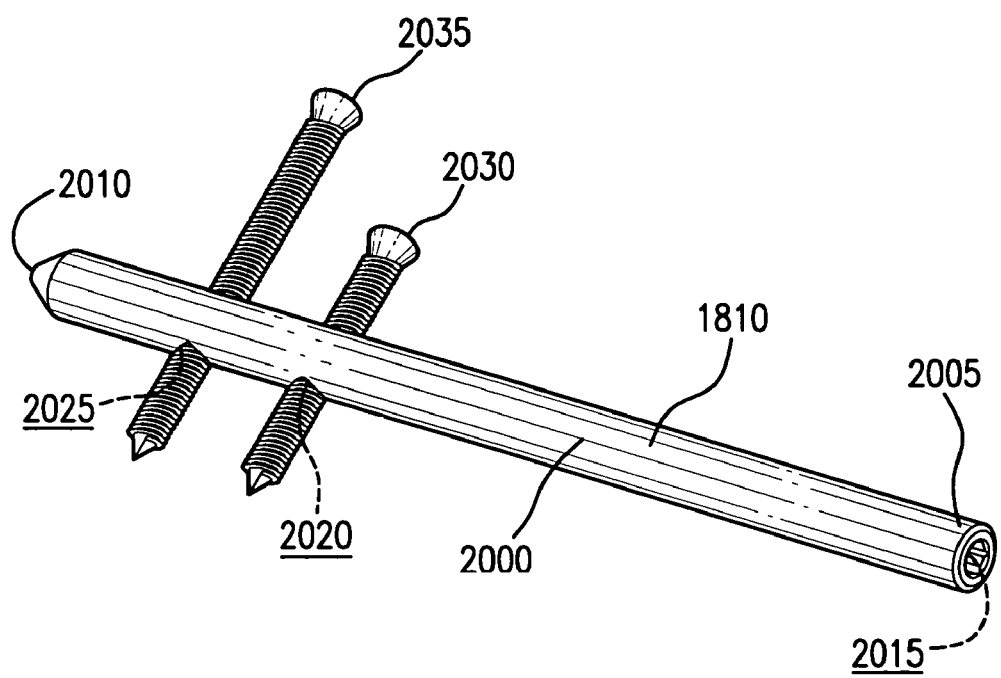
FIG. 20 is a perspective view of a proximal member used in the intramedullary fixation assembly shown in FIGS. 18-19 according to the alternate embodiment of the invention.

Referring to FIG. 20, proximal member 1810 has a generally cylindrical shaped body 2000 that is generally coextensive with length of the body 2000. Body 2000 extends from first end 2005 to a second tapered end 2010. Body 2000 is generally smooth and contains an internal aperture or cannula (not shown) that is longitudinally coextensive with body 2000. Moreover, end 2005 is generally circular and includes a generally hexagonal torque transmitting aperture 2015. In other non-limiting embodiments, a star-shaped aperture, a square-shaped aperture, or any other shaped aperture may be utilized without departing from the scope of the invention. Torque transmitting aperture 2015 is utilized to transmit torque from end 2005 to tapered end 2010 as end 2005 is rotated in a direction that causes end 2005 to rotate. The torque transmitting aperture 2015 is aligned with longitudinally coextensive internal aperture (not shown) to form a continuous opening from first end 2005 to second end 2010. The continuous opening is provided to interact with a guide wire (not shown), during insertion, by receiving the guide wire within the continuous opening in order to position and locate the proximal member 1810. In other non-limiting embodiments, the proximal member 1810 may be provided without an internal aperture (i.e., the proximal member 1810 is solid). The end of the proximal member 1810, the interconnecting end could be a morse taper, straight or of spherical shape.

Additionally, proximal member 1810 has a plurality of transverse apertures 2020 and 2025, with each aperture traversing the surface of body 2000 (i.e., penetrates body 2000). The plurality of apertures 2020 and 2025 are provided to receive a plurality of polyaxial locking screws 2030 and 2035 respectively in order to couple the proximal member 1810 to the talus bone 1835 (shown in FIG. 18) or other similar bones in the human foot 1805 (shown in FIG. 18). In other non-limiting embodiments, a non-locking screw may be utilized in lieu of the locking screws 2020 and 2025. It should be appreciated that the proximal member 1810 may be inserted at various angles such that the locking screws 2030 and 2035 may be inserted into the medial, dorsal, lateral, or plantar side or the talus bone 1835. Proximal member 1810 may be coated with an osteoconductive material, such as, for example, plasma spray or other similar types of porous materials that is capable of supporting or encouraging bone ingrowth into this material.

Figure 21A:
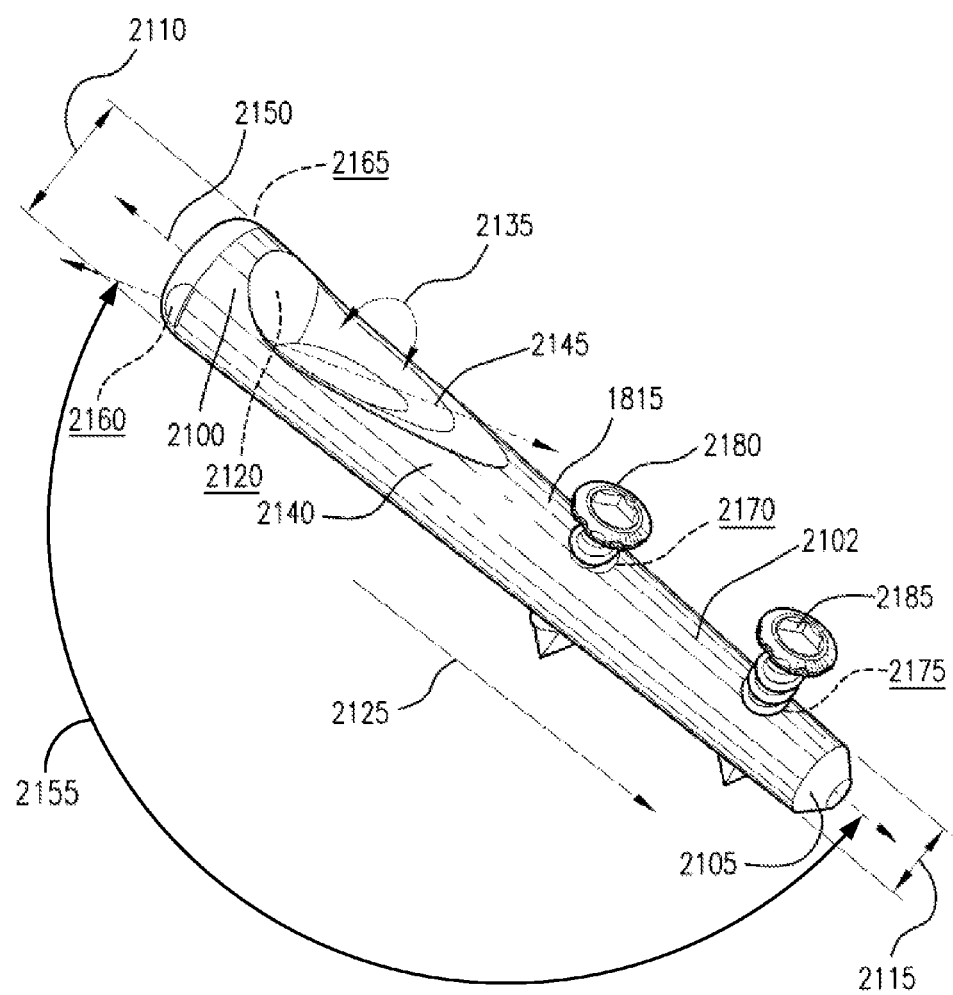
FIG. 21A is a perspective view of a distal member used in the intramedullary fixation assembly shown in FIGS. 18-19 according to the alternate embodiment of the invention.
Figure 21B:
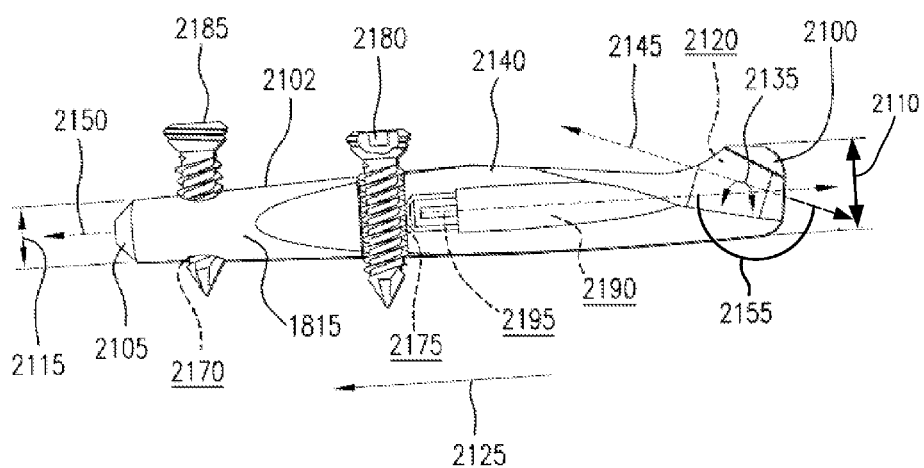
FIG. 21B is a perspective cross-sectional view of the distal member shown in FIG. 21A according to an alternate embodiment of the invention.
Figure 22:
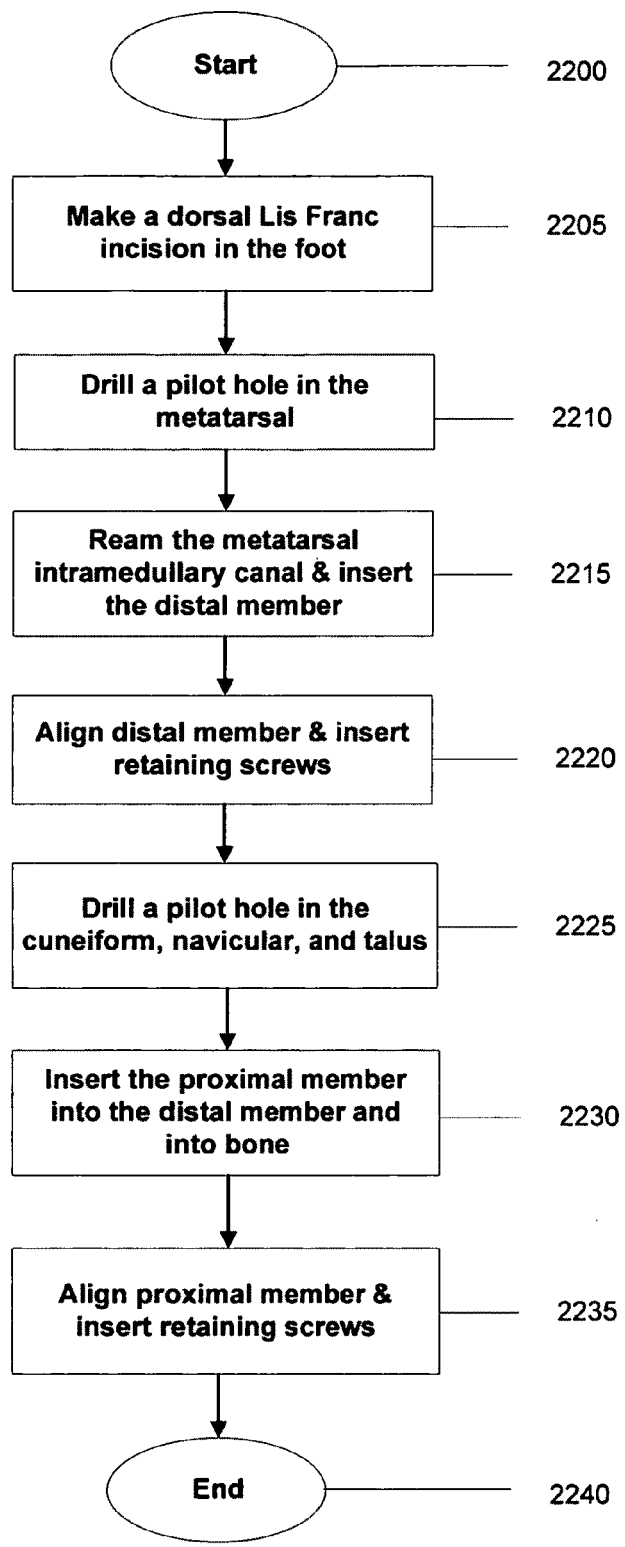
FIG. 22 is a flow chart illustrating the method of coupling the intramedullary fixation assembly shown in FIGS. 18-21B to bones in a patient's mid-foot region according to the alternate embodiment of the invention.

Referring to FIGS. 21A-21B, distal member 1815 has a generally tubular shaped body 2102 that tapers (or could be straight) from a first end 2100 to a second end 2105 (i.e. end 2100 has a diameter 2110 that is slightly larger than diameter 2115 of second end 2105). However, in another non-limiting embodiment, distal member 1815 has a constant width from first end 2100 to second end 2105. Distal member 1815 is aligned along longitudinal axis 2150.

First end 2100 has a plurality of substantially similar and opposed grooves 2160 and 2165 (shown in FIG. 21A). Grooves 2160 and 2165 are provided to receive an instrument, such as instrument 120, which was shown and described in FIG. 1. Further, first end 2100 is generally semi-spherical in shape and has an internal circular aperture 2120, which traverses end 2100 along direction 2125 (i.e., first end 2100 is generally "donut" shaped). Additionally, circular aperture 2120 is tapered at a slope 2135, which causes circular aperture 2120 to terminate at surface 2140 of distal member 1815. Further, slope 2135 is aligned along axis 2145, with axis 2145 forming an angle 2155 with longitudinal axis 2150 that determines the angle for arch restoration. Angle 2155 may be any angle greater than 90 degrees and less than 180 degrees. Aperture 2120 is provided to receive body 2000 of proximal member 1810 (shown in FIG. 20) as proximal member 1810 is slideably coupled to distal member 1815, while retaining end 2005 within aperture 2120. Tapered aperture 2120 when combined with end 2005 (shown in FIG. 20) creates a locked interference fit between proximal member 1810 and distal member 1815.

Additionally, distal member 1815 has a plurality of transverse apertures 2170 and 2175, with each penetrating the surfaces of body 2102. The plurality of apertures 2170 and 2175 are provided to receive a plurality of polyaxial locking screws 2180 and 2185 respectively in order to couple the distal member 1815 to the metatarsal bone 1820 (shown in FIG. 18) or other similar bones in the human foot 1805 (also shown in FIG. 18). In other non-limiting embodiments, a non-locking screw may be utilized in lieu of the locking screws 2180 and 2185. It should be appreciated that the distal member 1815 may be oriented at various angles in relation to the proximal member 1810 (shown in FIG. 20) so that the locking screws 2180 and 2185 may be inserted into the medial, dorsal, lateral, or plantar side or the metatarsal bone 1820.

Also as shown in FIG. 21B, body 2102 has a longitudinally coextensive aperture 2190, which emanates from aperture 2120, longitudinally traverses body 2102 in direction 2125 and terminates at second end 2105 to form a continuous opening or cannula. Aperture 2190 further includes a hexagonal shaped opening 2195, which is provided to receive a complementary shaped instrument to facilitate turning distal member 1815. In other non-limiting embodiments, a star-shaped aperture, a square-shaped aperture, or any other shaped aperture may be utilized.

As shown in FIGS. 18 and 20-22, the intramedullary fixation assembly 1800 may be utilized to reconstruct an arch through a rigid midfoot fusion in a human foot 1805. As shown, the method starts in step 2200 and proceeds to step 2205, whereby a Dorsal Lis Franc incision (i.e., mid-foot incision) (not shown) is made in foot 1805 in order to gain access to the joint. In step 2210, a pilot hole is drilled into the articular surface of metatarsal bone 1820. Next, in step 2215, the intramedullary canal is reamed and the distal member 1815 is inserted into the intramedullary canal (not shown) of the metatarsal bone 1820. In some non-limiting embodiments, the distal member 1815 may be inserted by impaction, by press fit, or substantially any other similar strategy or technique.

Next, in step 2220, the distal member 1815 is aligned with the use of an instrument (not shown) and polyaxial locking screws 2180 and 2185 are inserted into distal member 1815 through metatarsal bone 1820. Next, in step 2225, a pilot hole is drilled into the medial cuneiform bone 1825, and in one non-limiting example, the navicular bone 1830, and the talus bone 1835. Next, in step 2230, the proximal member 1810 is inserted into the distal member 1815 and the proximal member 1810 is hammered into the medial cuneiform bone 1825, the navicular bone 1830, and the talus bone 1835. Next, in step 2235, the proximal member 1810 is aligned with the use of an instrument (not shown) and polyaxial locking screws 2030 and 2035 are inserted through the talus bone 1835 and into the proximal member 1810. The method ends in step 2240.

It should be appreciated that a plurality of intramedullary fixation assemblies, such as intramedullary fixation assembly 1800, may be inserted into any of the rays of a foot 1805 in order to restore the natural anatomical shape of the foot 1805. It should also be appreciated that the intramedullary fixation assembly 1800 is delivered through a dorsal incision, thereby reducing the disruption to the plantar tissues and/or the metatarsal heads while at the same time minimizing the tension on the skin. This allows for improved wound closure, reduced operating room time, reduction in the number of incisions required and reduction in the total length of incisions. It should also be appreciated that the intramedullary fixation assembly 1800 may also be utilized-to restore any of the other bones in the human body. It should also be appreciated that in other non-limiting embodiments, the intramedullary assembly 1800 may be utilized with graft material (i.e., autograft, allograft or other biologic agent).

It should also be understood that this invention is not limited to the disclosed features and other similar method and system may be utilized without departing from the spirit and the scope of the invention.

While the invention has been described with reference to the preferred embodiment and alternative embodiments, which embodiments have been set forth in considerable detail for the purposes of making a complete disclosure of the invention, such embodiments are merely exemplary and are not intended to be limiting or represent an exhaustive enumeration of all aspects of the invention. The scope of the invention, therefore, shall be defined solely by the following claims. Further, it will be apparent to those of skill in the art that numerous changes may be made in such details without departing from the spirit and the principles of the invention. It should be appreciated that the invention is capable of being embodied in other forms without departing from its essential characteristics.

The invention claimed is:

1. An intramedullary fixation assembly for bone fusion, comprising:
    a first member comprising a first shaft extending along a first longitudinal axis, said first shaft having first and second ends, a retaining end near the first end, and a first aperture near the second end for receiving a first screw; and
    a second member comprising a second shaft terminating at a first terminal end and a second terminal end, and a first aperture at the first terminal end, a second longitudinal axis extending through the first aperture, the second shaft and the second terminal end, a bore extending through the first aperture and the second shaft on a third axis that extends between said first aperture and an exterior surface of said second shaft, and a second aperture near said second terminal end for receiving a second screw;
    wherein said first member is configured for coupling to said second member and provides for an interference fit with said second member.

2. The intramedullary fixation assembly of claim 1, wherein said retaining end comprises a circular end and wherein said first shaft includes a tapered end at said second end.

3. The intramedullary fixation assembly of claim 2, wherein said first member comprises a hexagonally-shaped aperture, a star-shaped aperture, or a square-shaped aperture disposed at said circular end.

4. The intramedullary fixation assembly of claim 3, wherein said hexagonally-shaped aperture, said star-shaped aperture, or said square-shaped aperture is provided to receive a complementary shaped end of an instrument.

5. The intramedullary fixation assembly of claim 1, wherein said second member includes an opening in said second shaft connecting to said bore, said opening being co-axially aligned with said second longitudinal axis.

6. The intramedullary fixation assembly of claim 5, wherein said opening includes a hexagonally shaped opening, a star-shaped opening, or a square-shaped opening partially disposed in said second shaft.

7. The intramedullary fixation assembly of claim 6, wherein each said hexagonally shaped opening, said star-shaped opening or said square-shaped opening is provided to receive a complementary shaped member.

8. The intramedullary fixation assembly of claim 5, wherein said opening has a hexagonal shape, a star shape, or a square shape.

9. The intramedullary fixation assembly of claim 5, wherein said opening is provided to receive a complementary shaped end of an instrument.

10. The intramedullary fixation assembly of claim 1, wherein said third axis forms an angle with said second longitudinal axis.

11. The intramedullary fixation assembly of claim 10, wherein said first member couples to said second member at said angle.

12. The intramedullary fixation assembly of claim 10, wherein said angle is in the range of about 90 degrees to about 180 degrees.

13. The intramedullary fixation assembly of claim 10, wherein said angle determines an angle for arch restoration.

14. The intramedullary fixation assembly of claim 10, wherein said angle determines an angle for restoration.

15. The intramedullary fixation assembly of claim 1, wherein said first shaft comprises a second aperture near the second end for receiving a third screw, and wherein said first and third screws are configured for insertion into a first bone to couple said first member to said first bone.

16. The intramedullary fixation assembly of claim 15, wherein said first and second apertures of said first member comprise apertures transverse to said first longitudinal axis for receiving said first and third screws.

17. The intramedullary fixation assembly of claim 1, wherein said second shaft comprises a third aperture near the second terminal end for receiving a third screw, wherein said second and third screws are configured for insertion into a second bone to couple said second member to said second bone.

18. The intramedullary fixation assembly of claim 17, wherein said second and third apertures of said second member comprise apertures transverse to said second longitudinal axis for receiving said second and third screws.

19. The intramedullary fixation assembly of claim 1, wherein said second shaft is tapered from said first end to said second end.

20. The intramedullary fixation assembly of claim 5, wherein said opening extends from said bore along said second longitudinal axis.

21. The intramedullary fixation assembly of claim 1, wherein said bore is tapered.

22. The intramedullary fixation assembly of claim 1, wherein said bore receives said first shaft of said first member, wherein said retaining end resides within said bore, and further wherein said retaining end abuts said first aperture of said second member at said terminal end.

23. The intramedullary fixation assembly of claim 1, wherein said first member couples to said second member by sliding into said bore until said retaining end of said first member abuts said first aperture of said second member.

24. An assembly for bone fusion, comprising:
    a first member comprising a first shaft extending along a first longitudinal axis, the first shaft having first and second ends, a retaining end near the first end, and at least one aperture near the second end for receiving a first screw; and
    a second member comprising a second shaft terminating at a first terminal end and a second terminal end, a first aperture at the first terminal end, a second longitudinal axis extending through the first aperture, the second shaft and the second terminal end, a bore extending through the first aperture and the second shaft on a third axis that extends between the first aperture and an exterior surface of the second shaft, and at least one aperture near said second terminal end for receiving a second screw;

wherein the first member is configured for coupling to the second member through the first aperture.

* * * * *